US010364279B2

(12) United States Patent
Tykocinski

(10) Patent No.: US 10,364,279 B2
(45) Date of Patent: Jul. 30, 2019

(54) PD-L1 AND PD-L2-BASED FUSION PROTEINS AND USES THEREOF

(71) Applicant: Thomas Jefferson University, Philadelphia, PA (US)

(72) Inventor: Mark L. Tykocinski, Merion Station, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 15/487,539

(22) Filed: Apr. 14, 2017

(65) Prior Publication Data

US 2018/0057561 A1  Mar. 1, 2018

Related U.S. Application Data

(63) Continuation of application No. 14/763,649, filed as application No. PCT/US2014/014171 on Jan. 31, 2014, now Pat. No. 9,657,082.

(60) Provisional application No. 61/759,287, filed on Jan. 31, 2013.

(51) Int. Cl.
  *C07K 14/705* (2006.01)
  *C07K 14/525* (2006.01)
  *A61K 38/00* (2006.01)

(52) U.S. Cl.
  CPC ...... *C07K 14/70521* (2013.01); *C07K 14/525* (2013.01); *C07K 14/70575* (2013.01); *A61K 38/00* (2013.01); *C07K 2319/30* (2013.01)

(58) Field of Classification Search
  None
  See application file for complete search history.

(56) References Cited

U.S. PATENT DOCUMENTS

| 7,569,663 | B2 | 8/2009 | Tykocinski et al. |
| 7,943,743 | B2 | 5/2011 | Korman et al. |
| 8,153,595 | B2 | 4/2012 | Chen |
| 8,168,179 | B2 | 5/2012 | Honjo et al. |
| 8,217,149 | B2 | 7/2012 | Irving et al. |
| 8,329,657 | B2 | 12/2012 | Tykocinski et al. |
| 8,354,509 | B2 | 1/2013 | Carven et al. |
| 8,741,295 | B2 | 6/2014 | Olive |
| 9,067,999 | B1 | 6/2015 | Honjo et al. |
| 2009/0239240 | A1 | 9/2009 | Chu |
| 2010/0048478 | A1 | 2/2010 | Tykocinski et al. |
| 2010/0055102 | A1 | 3/2010 | Langermann |
| 2010/0303811 | A1 | 12/2010 | Ochi |
| 2011/0041190 | A1 | 2/2011 | Tykocinski et al. |
| 2011/0200601 | A1 | 8/2011 | Stanley et al. |
| 2012/0027759 | A1 | 2/2012 | Chen et al. |
| 2012/0213781 | A1 | 8/2012 | Hilbert |
| 2013/0017199 | A1 | 1/2013 | Langermann |
| 2014/0044738 | A1 | 2/2014 | Langermann et al. |
| 2014/0199334 | A1 | 7/2014 | Sasikumar et al. |

FOREIGN PATENT DOCUMENTS

| EP | 2009022 A1 | 12/2008 |
| EP | 1297135 B1 | 1/2013 |
| WO | 2004069876 A2 | 8/2004 |
| WO | 2010144295 A1 | 12/2010 |
| WO | 2011109789 A2 | 9/2011 |

OTHER PUBLICATIONS

International Search Report and Written Opinion for PCT International Application No. PCT/US2014/014171 dated Apr. 17, 2014.
Dong, et al., "Costimulating aberrant T cell responses by B7-H1 autoantibodies in rheumatoid arthritis", J Clin Invest. 111(3), Feb. 2003, 363-370.
Dong, et al., "Tumor-associated B7-H1 promotes T-cell apoptosis: a potential mechanism of immune evasion", Nat Med. 8(8), Jun. 2002, 793-800.
Dranitzki-Elhalel, et al., "CD40.FasL inhibits human T cells: evidence for an auto-inhibitory loop-back mechanism", Int Immunol. 19(4), 2007, 355-363.
Gu, et al., "Different roles of PD-L1 and FasL in immunomodulation mediated by human placenta-derived mesenchymal stem cells", Hum Immunol. 74(3), Dec. 2012, 267-276.
Huang, et al., "CTLA-4-Fas ligand functions as a trans signal converter protein in bridging antigen-presenting cells and T cells", Int Immunol. 13(4), 2001, 529-539.
Kuipers, et al., "Contribution of the PD-1 ligands/PD-1 signaling pathway to dendritic cell-mediated CD4+ T cell activation", Eur J Immunol. 36(9), 2006, 2472-2482.
Orbach, et al., "CD40-FasL and CTLA-4-FasL fusion proteins induce apoptosis in malignant cell lines by dual signaling", Am J Pathol.177(6), 2010, 3159-3168.
Podojil, et al., "Targeting the B7 family of co-stimulatory molecules: successes and challenges", BioDrugs. 27(1), 2013, 1-13.

*Primary Examiner* — John D Ulm
(74) *Attorney, Agent, or Firm* — Saul Ewing Arnstein & Lehr LLP; Kathryn Doyle; Debora Plehn-Dujowich

(57) ABSTRACT

Provided are fusion proteins comprising a first domain and a second domain, wherein the first domain comprises a polypeptide that binds to and triggers PD-1 and the second domain comprises a polypeptide that binds to and triggers a TRAIL receptor or Fas. In some embodiments, the polypeptide that binds to and triggers PD-1 comprises at least a portion of the extracellular domain of PD-L1 or PD-L2 and the second domain comprises at least a portion of the extracellular domain of TRAIL or Fas ligand. Also provided are methods for treating autoimmune, alloimmune or inflammatory diseases, and methods for treating cancer, using the fusion proteins.

9 Claims, No Drawings
Specification includes a Sequence Listing.

PD-L1 AND PD-L2-BASED FUSION PROTEINS AND USES THEREOF

CROSS-REFERENCE TO RELATED APPLICATION

This application is a continuation of, and claims priority to, U.S. patent application Ser. No. 14/763,649, filed Jul. 27, 2015, now issued as U.S. Pat. No. 9,657,082, which is a 35 U.S.C. § 371 national phase application from, and claims priority to, International Application No. PCT/US2014/014171, filed Jan. 31, 2014, and published under PCT Article 21(2) in English, which claims the benefit of U.S. Provisional Application No. 61/759,287, filed Jan. 31, 2013, all of which applications are incorporated herein by reference in their entireties.

SEQUENCE LISTING

The instant application contains a Sequence Listing which has been submitted in ASCII format via EFS-Web and is hereby incorporated by reference in its entirety.

FIELD OF THE INVENTION

The present invention relates to fusion proteins comprising a first domain and a second domain, wherein the first domain is a polypeptide that binds to and triggers PD-1, such as PD-L1 or PD-L2, and the second domain is a polypeptide that binds to and triggers a TRAIL receptor or Fas, such as TRAIL or Fas ligand.

BACKGROUND OF THE INVENTION

A complex interplay of positive and negative signals regulates T cell activation and maintenance of T cell effector function. Members of the TNF ligand/TNF receptor superfamily figure prominently in this matrix of signals, bridging cells of the immune system, as well as with cells of other organ systems. In so doing, TNF superfamily members contribute to both tissue homeostasis and pathogenesis, via effects on cell survival and death, cellular differentiation, and inflammation. From the standpoint of autoimmune pathogenesis, an interesting member of the TNF ligand superfamily is TNF-related apoptosis-inducing ligand (TRAIL).

TRAIL binds to a number of different cognate receptors of the TNF receptor superfamily, some leading to triggering of intracellular signaling pathways and others simply acting as decoy receptors. The triggering receptors in humans are TRAIL-R1, TRAIL-R2, and osteoprotegrin, and in mice the sole triggering receptor is DR5. Virtually all cells of the immune system (T lymphocytes, B lymphocytes, natural killer cells, dendritic cells, monocytes, granulocytes) upregulate surface TRAIL and/or release soluble TRAIL stored in secretory vesicles in response to interferon and other activation signals. TRAIL inhibits autoimmunity in several animal models. Evidence for TRAIL's capacity to inhibit experimental autoimmune encephalitis (EAE), a murine model for multiple sclerosis (MS), has come from experiments invoking TRAIL−/− knockout mice, soluble TRAIL receptor (sDR5) or neutralizing anti-TRAIL mAb capable of blocking TRAIL function, and embryonic stem cell-derived dendritic cells co-expressing TRAIL and pathogenic MOG (myelin oligo-dendrocyte glycoprotein peptide). Interestingly, in MS patients, soluble TRAIL has emerged as a response marker for IFN-β therapy, with those most likely to respond to treatment showing early and sustained soluble TRAIL induction after therapy. Yet, TRAIL's impact on MS/EAE may be more complex, for example, the suggestion that TRAIL may promote brain cell apoptosis. Both TRAIL and FasL have been implicated in inhibition of T cells and the induction of apoptosis in T cells.

Apoptosis or programmed cell death (PCD) is a form of cell death which is essential for the regulation of cellular homeostasis. In the immune system, Fas (CD95) receptor and its ligand, FasL (CD95L), participate in various processes involved in the induction of apoptosis, including immune cell-mediated cytotoxicity, and in the regulation of cellular immune responses. FasL is a member of the tumor necrosis factor superfamily and is expressed by a restricted subset of immune cells, including monocytes, NK cells, and activated B and T cells. On the cell surface, FasL is oriented as a type II membrane protein with trimeric complexes. Metalloproteinase cleavage of membrane-associated FasL releases soluble FasL (sFasL) trimmers from the membrane. The FasL molecule triggers Fas-dependent PCD.

One of the newer pathways that provide costimulatory and inhibitory second signals to T cells is represented by the programmed death 1 (PD-1; also known as CD279) receptor and its ligands, PD-L1 (B7-H1; CD274) and PD-L2 (B7-DC; CD273). PD-1 is a member of the CD28/CTL4 family that is expressed on activated, but not resting T cells (Nishimura et al. (1996) *Int. Immunol.* 8:773). Ligation of PD-1 by its ligands mediates an inhibitory signal that results in reduced cytokine production, and reduced T cell survival (Nishimura et al. (1999) *Immunity* 11:141; Nishimura et al. (2001) *Science* 291:319, Chemitz et al. (2004) *J. Immunol.* 173:945).

PD-L1 is a B7 family member that is expressed on many cell types, including antigen presenting cells (APCs) and activated T cells (Yamazaki et al. (2002) *J. Immunol.* 169:5538). PD-L1 binds to both PD-1 and B7-1. Both binding of T-cell expressed B7-1 by PD-L1 and binding of T-cell-expressed PD-L1 by B7 result in T cell inhibition (Butte et al. (2007) *Immunity* 27:111). There is also evidence that, like other B7 family members, PD-L1 can also provide costimulatory signals to T cells (Subudhi et al. (2004) *J. Clin. Invest.* 113:694; Tamura et al. (2001) *Blood* 97:1809).

PD-L2 is a B7 family member expressed on various APCs, including dendritic cells, macrophages and bone-marrow derived mast cells (Zhong et al. (2007) *Eur. J. Immunol.* 37:2405). APC-expressed PD-L2 is able to both inhibit T cell activation through ligation of PD-1 and costimulate T cell activation, through a PD-1 independent mechanism (Shin et al. (2005) *J. Exp. Med.* 201:1531). In addition, ligation of dendritic cell-expressed PD-L2 results in enhanced dendritic cell cytokine expression and survival (Radhakrishnan et al. (2003) *J. Immunol.* 37:1827; Nguyen et al. (2002) 1 Exp. Med. 196:1393). The structure and expression of PD-1, PD-L1 and PD-L2, as well as signaling characteristics and functions of these molecules in the context of regulating T cell activation and tolerance (e.g., therapeutic effects) are reviewed in greater detail in Kier et al. (2008) *Ann. Rev. Immunol.* 26:677, which is herein incorporated by reference in its entirety.

SUMMARY OF THE INVENTION

Provided is a fusion protein comprising a first domain and a second domain, wherein the first domain comprises a polypeptide that binds to and triggers PD-1 and the second domain comprises a polypeptide that binds to and triggers a TRAIL receptor or Fas. In some embodiments, the polypeptide that binds to and triggers PD-1 comprises at least a portion of the extracellular domain of PD-L1 or PD-L2 and the second domain comprises at least a portion of the extracellular domain of TRAIL or Fas ligand. In further embodiments, the fusion protein comprises at least a portion of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12.

In certain embodiments, provided is a fusion protein according to any one of the preceding embodiments, comprising a first domain and a second domain, wherein the first domain comprises a portion of the extracellular domain of PD-L1 or PD-L2 comprising at least 20 contiguous amino acids of said extracellular domain, and the second domain comprises a portion of the extracellular domain of TRAIL or Fas ligand comprising at least 20 contiguous amino acids of said extracellular domain, and the first and second domain are connected via an optional linker. In some embodiments, the first domain comprises human PD-L1 or human PD-L2, or a fragment thereof capable of binding to and triggering PD-1, and the second domain comprises human TRAIL or human Fas ligand, or a fragment thereof. In further embodiments, the first domain and the second domain are connected via a linker. In yet further embodiments, the linker comprises a protein linker.

Further provided is the fusion protein of any one of the preceding embodiments, in a pharmaceutically acceptable carrier.

Also provided is a pharmaceutical composition comprising the fusion protein of any one of the preceding embodiments.

Further provided is a method of treating an autoimmune, alloimmune or inflammatory disease in a patient comprising administering the fusion protein of any one of the preceding embodiments to a patient in need of such treatment. In some embodiments, the autoimmune disease is multiple sclerosis. In further embodiments of the method, the administration is parenteral.

Also provided is a method of inhibiting proliferation and differentiation of T cells, B cells, mast cells, antigen presenting cells, dendritic cells or NK cells in a patient, the method comprising the step of administering the fusion protein of any one of the preceding embodiments to a patient in need of such treatment.

Also provided is a method of treating cancer in a patient comprising administering the fusion protein of any one of the preceding embodiments to a patient in need of such treatment.

Also provided is a method of treating autoimmune disease, alloimmune disease, inflammatory disease or cancer in a patient by administering to said patient an effective amount of a genetic sequence encoding the fusion protein of any one of the preceding embodiments.

Further provided is a fusion protein of any one of the preceding embodiments, for use in (i) medicine, (ii) treating an autoimmune, alloimmune or inflammatory, (iii) inhibiting proliferation and differentiation of T cells, B cells, mast cells, antigen presenting cells, dendritic cells or NK cells, or (iii) treating cancer. Also provided is a genetic sequence encoding a fusion protein of any one of the preceding embodiments, for use in medicine, or for use in treating autoimmune disease, alloimmune disease, inflammatory disease or cancer.

DEFINITIONS

As used in the specification and the appended claims, the singular forms "a," "an" and "the" include plural referents unless the context clearly dictates otherwise.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

As used herein, the term "fusion protein" or fusion polypeptide is a polypeptide comprised of at least two polypeptides and optionally a linking sequence, and that are operatively linked into one continuous protein. The two polypeptides linked in a fusion protein are typically derived from two independent sources, and therefore a fusion protein comprises two linked polypeptides not normally found linked in nature. Typically, the two polypeptides can be operably attached directly by a peptide bond.

As used herein, "trigger" with respect to a receptor, such as TRAIL receptor or Fas, refers to the biological change that occurs upon ligation of the receptor by an agonist ligand. Biological changes that can occur when a receptor is triggered include, but are not limited to, one or more of: receptor interaction with one or more intracellular adaptors and effector molecules; induction of a signaling cascade; modified expression of molecules; release of cytokines and/or chemokines; activation of caspases; activation of transcription factors; changes in protein modification such as a phosphorylation; activation of signal transduction pathways such as NF-κB and P13K; induction of downstream effects on transcriptional, translational, and post-translational control mechanisms affecting one or more genes and/or proteins expressed by the cell.

As used herein, the term "immune disease" and like terms means a disease, disorder or condition caused by the immune system of an animal, including autoimmune disorders. Immune disorders include those diseases, disorders or conditions that have an immune component and those that are substantially or entirely immune system-mediated.

As used herein, the term "alloimmune disease" refers to when there is a host immune response to foreign antigens of another individual (for example, major or minor histocompatibility alloantigens), for example when there is a host-versus-graft rejection, or alternatively when there is graft-versus-host disease, wherein engrafted immune cells mediate deleterious effects against the host receiving the graft.

As used herein, the term "autoimmune disease" refers to a disease, disorder or condition that results from an aberrant immune response that results from the failure of an organism in recognizing its own constituent parts as self, which allows an immune response against its own cells and tissues.

As used herein, an "inflammatory disease" means a disease, disorder or condition characterized by inflammation of body tissue or having an inflammatory component, typically due to infiltration of tissue by immune cells. These disorders include both local inflammatory responses and systemic inflammation.

The term "operably linked," as used herein, indicates that two molecules (e.g., polypeptides) are attached so as to each retain biological activity. Two molecules are "operably linked" whether they are attached directly or indirectly (e.g., via a linker).

The term "linker," as used herein, refers to a peptide that is optionally located between two amino acid sequences in the fusion protein of the invention.

As used herein, "biologically active" or "immunologically active" as applied to fusion proteins refers to fusion proteins according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild type proteins which are the building blocks of the fusion proteins of the present invention.

As used herein, a "deletion" in an amino acid sequence or polypeptide is defined as a change in amino acid sequence in which one or more amino acid residues are absent as compared to the wild-type protein.

As used herein an "insertion" or "addition" in an amino acid sequence or polypeptide is a change in an amino acid sequence that has resulted in the addition of one or more amino acid residues as compared to the wild-type protein.

As used herein "substitution" in an amino acid sequence or polypeptide results from the replacement of one or more amino acids by different amino acids, respectively, as compared to the wild-type protein.

As used herein, a "trimerization domain" refers to an amino acid sequence within a polypeptide that promotes assembly of the polypeptide into trimers. For example, a trimerization domain can promote assembly of a protein into trimers via associations with other trimerization domains (of additional polypeptides with the same or a different amino acid sequence). The term is also used to refer to a polynucleotide that encodes such a peptide or polypeptide.

As used herein, the term "variant" with respect to an amino acid sequence or polypeptide means any polypeptide having a substitution of, deletion of or addition of one (or more) amino acid from or to the sequence, including allelic variations, as compared with the wild-type protein, so long as the resultant variant fusion protein retains at least 75%, 80%, 85%, 90%, 95%, 96%, 97%, 98%, 99% or more of the biological or immunologic activity as compared to the wild-type proteins as used in the present invention. Additionally, while in general it is desirable for variants to show enhanced ability for binding to a given molecule, in some embodiments variants may be designed with slightly reduced activity as compared to other fusion proteins of the invention, for example, in instances in which one would purposefully want to attenuate activity, for example, to diminish neurotoxicity. Moreover, variants or derivatives can be generated that would bind more selectively to one of the TRAIL receptor variants (there are four TRAIL receptors in humans). Furthermore, variants or derivatives can be generated that would have altered multimerization properties. When engineering variants, this could be done for either the entire TRAIL extracellular domain, or for that component of the extracellular domain that is incorporated within the fusion protein itself.

In one embodiment, variants of the fusion proteins of the present invention will have at least 80% or greater sequence identity or homology, as those terms are understood in the art, to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12, more preferably at least 85%, 86%, 87%, 88%, 89%, 90%, 91%, 92%, 93%, 94%, 95%, 96%, 97%, 98%, or even 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12.

Sequence identity or homology can be determined using standard techniques known in the art, such as the Best Fit sequence program described by Devereux et al., *Nucl. Acid Res.* 12:387-395 (1984) or the BLASTX program (Altschul et al., *J. Mol. Biol.* 215, 403-410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids.

Additionally, while in general it is desirable for variants to show enhanced ability for binding to a given molecule, in some embodiments variants may be designed with slightly reduced activity as compared to other fusion proteins of the invention, for example, in instances in which one would purposefully want to attenuate activity, for example, to diminish neurotoxicity. Moreover, variants or derivatives can be generated that would bind more selectively to one of the TRAIL receptor variants (there are two TRAIL receptors in humans that induce apoptosis).

Furthermore, variants or derivatives can be generated that would have altered multimerization properties. When engineering variants, this could be done for either the entire TRAIL extracellular domain, or for that component of the extracellular domain that is incorporated within the fusion protein itself.

Preferably, variants or derivatives of the fusion proteins of the present invention maintain the hydrophobicity/hydrophilicity of the amino acid sequence. Conservative amino acid substitutions may be made, for example from 1, 2 or 3 to 10, or 30 substitutions provided that the modified sequence retains the ability to act as a fusion protein in accordance with present invention. Amino acid substitutions may include the use of non-naturally occurring analogues, for example to increase blood plasma half-life.

Conservative substitutions are known in the art, for example according to the table below. Amino acids in the same block in the second column and preferably in the same line in the third column may be substituted for each other:

| ALIPHATIC | Non-polar | GAPILV |
|---|---|---|
| | Polar- | CSTM |
| | Uncharged | NQ |
| | Polar-charged | DE |
| | | KR |
| AROMATIC | | HFWY |

The term "derivative" as used herein in relation to the amino acid sequence means chemical modification of a fusion protein of the invention.

Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a fusion protein conjugated with polyethylene glycol (PEG), or addition of PEG during chemical synthesis of a polypeptide of the invention.

Modifications of polypeptides or portions thereof can also include reduction/alkylation; chemical coupling to an appropriate carrier or mild formalin treatment.

Other derivatives of the fusion proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylations site(s) are added or glycosylation sites are deleted or disabled. Furthermore, if no glycosylation is desired, the proteins can be produced in a prokaryotic host expression system.

Variants and/or derivatives of the fusion proteins of the invention can be prepared by chemical synthesis or by using site-directed mutagenesis (Gillman et al., Gene 8:81 (1979); Roberts et at, Nature 328:731 (1987) or Innis (Ed.), 1990, PCR Protocols: A Guide to Methods and Applications, Academic Press, New York, N.Y.) or the polymerase chain reaction method (PCR; Saiki et al, Science 239:487 (1988)), as exemplified by Daugherty et at (Nucleic Acids Res. 19:2471 (1991)) to modify nucleic acids encoding the complete receptors.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein".

As used herein, a polypeptide is "soluble" when it lacks any transmembrane domain or peptide domain that anchors or integrates the polypeptide into the membrane of a cell expressing such polypeptide. In particular, the soluble proteins useful as components in the fusion protein of the invention may exclude transmembrane and intracellular domains. The soluble proteins may comprise substantially all of an ectodomain or may comprise a fragment thereof possessing the required agonist function, e.g., a functional fragment.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, a "therapeutically effective amount" is the amount of a composition sufficient to provide a beneficial effect to a mammal to which the composition is administered. An therapeutically effective amount of a fusion protein of the invention is an amount that will ameliorate one or more of the well known parameters that characterize medical conditions caused by autoimmune disease, alloimmune disease, inflammatory disease or cancer. Many such parameters and conditions have been described and are well known to the skilled artisan. A therapeutically effective amount, in the context of a cancer, for example, will be the amount of fusion protein that is sufficient to accomplish one or more of the following: decrease the severity of symptoms; decrease tumor size; decrease rate of tumor growth; decrease the duration of disease exacerbations; increase the frequency and duration of disease remission/symptom-free periods; prevent fixed impairment and disability; and/or prevent/attenuate chronic progression of the disease.

"Treating" or "treatment" refers to therapeutic treatment, wherein the object is to prevent or slow down (lessen) the targeted pathologic condition or disorder. A subject is "treated" if: after receiving a therapeutic amount of a fusion protein of the invention according to the methods of the present invention, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Treatment can achieve a complete response, defined as disappearance of all signs of cancer, or a partial response, wherein the size of the tumor is decreased, preferably by more than 50%, more preferably by 75%. A patient is also considered treated if the patient experiences a stabilization of disease.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein with respect to polynucleotides means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "TRAIL receptor" as used herein refers to a receptor that binds to TRAIL ligand and induces or triggers apoptosis. In some embodiments, the TRAIL receptor is DR4 (TRAILR1). In some embodiments, the TRAIL receptor is DR5 (TRAILR2). The term "TRAIL receptor" as used herein does not refer to the receptors DcR1 (TRAILR3) and DcR2 (TRAILR4). DcR1 does not contain a cytoplasmic domain, and DcR2 (TRAILR4) contains a truncated death domain. DcR1 functions as a TRAIL-neutralizing decoy-receptor. The cytoplasmic domain of DcR2 is functional and activates NFkappaB. In cells expressing DcR2, TRAIL binding therefore activates NFkappaB, leading to transcription of genes known to antagonize the death signaling pathway and/or to promote inflammation.

The term "Fas" or "Fas receptor" as used herein refers to a receptor that binds to Fas ligand (FasL) and induces or triggers apoptosis.

As used herein in the specification and claims, including as used in the examples and unless otherwise expressly specified, all numbers may be read as if prefaced by the word "about", even if the term does not expressly appear.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DETAILED DESCRIPTION OF THE INVENTION

The present invention provides, in one aspect, a fusion protein that acts on the PD-1 and TRAIL or Fas signaling axis, for example a fusion protein comprising a first domain that comprises PD-L1 or PD-L2; and a second domain that comprises a polypeptide that binds to and triggers a TRAIL receptor or a Fas receptor. In particular, the first domain comprises at least a portion of the extracellular domain of PD-L1 or PD-L2, and the second domain comprises at least a portion of a polypeptide that can bind to TRAIL receptor or Fas receptor and direct inhibitory signals through cognate receptors on T cells or other cells bearing a TRAIL receptor or a Fas receptor.

The first domain and the second domain need be in no particular order. In some preferred embodiments, the first domain is at the N-terminus of the protein, and the second domain is at the C-terminus of the protein. In some embodiments, the second domain is at the N-terminus of the protein, and the second domain is at the C-terminus of the protein.

The present invention provides novel fusion proteins useful for treating certain immune and inflammatory disorders. In the setting of autoimmune, alloimmune and inflammatory diseases, the fusion protein of this invention can reduce autoimmune, alloimmune and inflammatory manifestations by one or more mechanisms. For example, the fusion protein of this invention can bind to an activated immune cell, such as an activated T cell, that co-expresses on its surface a receptor for the first domain of the fusion protein, such as PD-1, as well as a receptor for the second domain of the fusion protein, such as a TRAIL receptor or a Fas receptor. Through this binding event, the receptors for the first domain and for the second domain of the fusion protein may be co-triggered and thereby the death of the activated immune cell may be induced.

Alternatively, the fusion protein of the present invention may mediate its activity by spanning two neighboring cells. For example, a PD-L1 or PD-L2 containing fusion protein can bind to the B7-1 costimulator on an antigen-presenting cell, thereby interfering with its costimulatory, immune-activating function. In addition, a PD-L1 or PD-L2-containing fusion protein can bind to PD-1 on an antigen-presenting cell and thereby elicit immunosuppressive cytokine production. Furthermore, once anchored to a cell in one of these ways (that is, via binding to B7-1 or to PD-1), the apoptosis-inducing TRAIL ligand or Fas ligand, now membrane-anchored, can induce cell death in a neighboring activated T cell, or, in the case of an antigen-presenting cell bearing receptors for TRAIL ligand or Fas ligand, autoinhibition (for example, auto-apoptosis) of the cell. Thus, the fusion proteins act to treat disease by causing a reduction in certain immune cells.

Suitable first domains in the context of the PD-1 and TRAIL/Fas signaling axis include, for example, PD-L1 or PD-L2 protein itself, variants or derivatives of PD-L1 or PD-L2 protein, or other polypeptides or proteins that are specifically designed to trigger the PD-1 receptor, such as agonistic anti-PD-1 Ab, and variants and/or derivatives of these. Preferably, the first domain of the fusion protein in this embodiment comprises at least a portion of the extracellular domain of PD-L1 or PD-L2 protein, specifically that portion which is necessary for binding to a PD-1 receptor. Variants of the wild-type form of the extracellular domain of the PD-L1 or PD-L2 protein, or the portion of the extracellular domain responsible for PD-1 receptor binding and triggering, are also included in the present invention, so long as the variant provides a similar level of biological activity as the wild-type protein.

Accordingly, the term "polypeptide that binds to and triggers PD-1 receptor" as used herein includes, for example, PD-L1 or PD-L2 protein; the extracellular domain of PD-L1 or PD-L2 protein; a polypeptide which comprises at least a portion of the extracellular domain of PD-L1 or PD-L2 protein, which portion is responsible for binding to a PD-1 receptor; antibodies to a PD-1 or B7-1 receptor; lipocalins engineered to bind to a PD-1 receptor; and variants and/or derivatives of any of these. The term "PD-1" is understood to embrace polypeptides corresponding to the complete amino acid sequence of the PD-1 protein, including the cytoplasmic, transmembrane and extracellular domains, as well as polypeptides corresponding to smaller portions of the protein, such as the extracellular domain, or a portion of the extracellular domain. In one embodiment the first domain of the PD-L1/TRAIL, PD-L2/TRAIL, PD-L1/FasL or PD-L2/FasL signaling pair comprises at least a portion of the extracellular domain of the human PD-L1 or PD-L2 protein.

PD-L1 and PD-L2 have two IgSF domains: one IgV and one IgC domain. In some embodiments, the polypeptide that binds to and triggers PD-1 receptor comprises at least 20 contiguous amino acids of the IgV domain of PD-L1 or PD-L2. In some embodiments, the polypeptide that binds to and triggers PD-1 receptor comprises the entire IgV domain of PD-L1 or PD-L2. In some embodiments, the polypeptide that binds to and triggers PD-1 receptor comprises at least 20 contiguous amino acids of the IgV and the IgC domain of PD-L1 or PD-L2. In some embodiments, the polypeptide that binds to and triggers PD-1 receptor comprises the entire IgV and IgC domains of PD-L1 or PD-L2. The human PD-L1 IgV domain covers amino acids 19-127 and the IgC domain amino acids covers amino acids 153-210. The human PD-L2 IgV domain covers amino acids 21-118 and the IgC domain covers amino acids 137-193.

Suitable second domains in the context of the PD-1/TRAIL signaling axis include, for example, the TRAIL protein itself, variants or derivatives of the TRAIL protein, or other polypeptides or proteins that are specifically designed to inhibit activation of T cells or other cells and/or induce apoptosis through binding to and triggering the TRAIL receptor, such as agonistic anti-TRAIL receptor Ab, and variants and/or derivatives of these. Preferably, the second domain of the fusion protein in this embodiment comprises at least a portion of the extracellular domain of the TRAIL protein, specifically that portion which is necessary for binding to a TRAIL receptor. Variants of the wild-type form of the extracellular domain of the TRAIL protein, or the portion of the extracellular domain responsible for TRAIL receptor binding and triggering, are also included in the present invention, so long as the variant provides a similar level of biological activity as the wild-type protein.

Accordingly, the term "polypeptide that binds to a TRAIL receptor" as used herein includes, for example, the TRAIL protein; the extracellular domain of the TRAIL protein; a polypeptide which comprises at least a portion of the extracellular domain of the TRAIL protein, which portion is responsible for binding to a TRAIL receptor; antibodies to a TRAIL receptor, or derivatives thereof; lipocalins engineered to bind to a TRAIL receptor; and variants and/or derivatives of any of these. The term "TRAIL" is understood to embrace polypeptides corresponding to the complete amino acid sequence of the TRAIL protein, including the cytoplasmic, transmembrane and extracellular domains, as well as polypeptides corresponding to smaller portions of the protein, such as the extracellular domain, or a portion of the extracellular domain. In one embodiment the second domain of the PD-L1/TRAIL or PD-L2/TRAIL signaling pair comprises at least a portion of the extracellular domain of the human TRAIL protein.

In one embodiment, the fusion protein comprises a PD-L1/TRAIL fusion protein. In an embodiment, the PD-L1/TRAIL fusion protein comprises the fusion protein having the amino acid sequence SEQ ID NO: 1. The underlined and bolded amino acids correspond to the second domain, which domain comprises a portion of TRAIL protein.

```
                                            (SEQ ID NO: 1)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIETIS TVQEKQQNI

SPLVRERGPQ RVAAHITGTR GRSNTLSSPN SKNEKALGRK

INSWESSRSG HSFLSNLHLR NGELVIHEKG FYYIYSQTYF

RFQEEIKENT KNDKQMVQYI YKYTSYPDPI LLMKSARNSC

WSKDAEYGLY SIYQGGIFEL KENDRIFVSV TNEHLIDMDH

EASFFGAFLV G
```

In another embodiment, the PD-L1/TRAIL fusion protein comprises the fusion protein having the amino acid sequence SEQ ID NO: 2. The underlined and bolded amino acids correspond to the second domain, which comprises a portion of TRAIL protein.

```
                                            (SEQ ID NO: 2)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIRGPQ RVAAHITGTR

GRSNTLSSPN SKNEKALGRK INSWESSRSG HSFLSNLHLR

NGELVIHEKG FYYIYSQTYF RFQEEIKENT KNDKQMVQYI

YKYTSYPDPI LLMKSARNSC WSKDAEYGLY SIYQGGIFEL

KENDRIFVSV TNEHLIDMDH EASFFGAFLV G
```

In another embodiment, the PD-L1/TRAIL fusion protein comprises the fusion protein having the amino acid sequence SEQ ID NO: 3. The underlined and bolded amino acids correspond to the second domain, which comprises a portion of TRAIL protein. The bolded amino acids that are not underlined correspond to a linker.

```
                                            (SEQ ID NO: 3)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIGDPL VTAASVLEFG

GSGGGSEGGG SEGGGSEGGG SDIETISTVQ EKQQNISPLV

RERGPQRVAA HITGTRGRSN TLSSPNSKNE KALGRKINSW

ESSRSGHSFL SNLHLRNGEL VIHEKGFYYI YSQTYFRFQE

EIKENTKNDK QMVQYIYKYT SYPDPILLMK SARNSCWSKD

AEYGLYSIYQ GGIFELKEND RIFVSVTNEH LIDMDHEASF

FGAFLVG
```

In another embodiment, the PD-L1/TRAIL fusion protein comprises the fusion protein having the amino acid sequence SEQ ID NO: 4. The underlined and bolded amino acids correspond to the second domain, which comprises a portion of TRAIL protein. The bolded amino acids that are not underlined correspond to a linker.

```
                                            (SEQ ID NO: 4)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIGDPL VTAASVLEFG

GSGGGSEGGG SEGGGSEGGG SDIRGPQRVA AHITGTRGRS

NTLSSPNSKN EKALGRKINS WESSRSGHSF LSNLHLRNGE

LVIHEKGFYY IYSQTYFRFQ EEIKENTKND KQMVQYIYKY

TSYPDPILLM KSARNSCWSK DAEYGLYSIY QGGIFELKEN

DRIFVSVTNE HLIDMDHEAS FFGAFLVG
```

In one embodiment, the fusion protein comprises a PD-L2/TRAIL fusion protein. In an embodiment, the PD-L2/TRAIL fusion protein comprises the fusion protein having the amino acid sequence SEQ ID NO: 5. The underlined and bolded amino acids correspond to the second domain, which comprises a portion of TRAIL protein.

```
                                            (SEQ ID NO: 5)
MIFLLLMLSL ELQLHQIAAL FTVTVPKELY IIEHGSNVTL

ECNFDTGSHV NLGAITASLQ KVENDTSPHR ERATLLEEQL
```

```
                                            -continued
PLGKASFHIP  QVQVRDEGQY  QCIIIYGVAW  DYKYLTLKVK

ASYRKINTHI  LKVPETDEVE  LTCQATGYPL  AEVSWPNVSV

PANTSHSRTP  EGLYQVTSVL  RLKPPPGRNF  SCVFWNTHVR

ELTLASIDLQ  SQMEPRTHPT  ETISTVQEKQ  QNISPLVRER

GPQRVAAHIT  GTRGRSNTLS  SPNSKNEKAL  GRKINSWESS

RSGHSFLSNL  HLRNGELVIH  EKGFYYIYSQ  TYFRFQEEIK

ENTKNDKQMV  QYIYKYTSYP  DPILLMKSAR  NSCWSKDAEY

GLYSIYQGGI  FELKENDRIF  VSVTNEHLID  MDHEASFFGA

FLVG
```

In another embodiment, the PD-L2/TRAIL fusion protein comprises the fusion protein having the amino acid sequence SEQ ID NO: 6. The underlined and bolded amino acids correspond to the second domain, which comprises a portion of TRAIL protein.

```
                                            (SEQ ID NO: 6)
MIFLLLMLSL  ELQLHQIAAL  FTVTVPKELY  IIEHGSNVTL

ECNFDTGSHV  NLGAITASLQ  KVENDTSPHR  ERATLLEEQL

PLGKASFHIP  QVQVRDEGQY  QCIIIYGVAW  DYKYLTLKVK

ASYRKINTHI  LKVPETDEVE  LTCQATGYPL  AEVSWPNVSV

PANTSHSRTP  EGLYQVTSVL  RLKPPPGRNF  SCVFWNTHVR

ELTLASIDLQ  SQMEPRTHPT  RGPQRVAAHI  TGTRGRSNTL

SSPNSKNEKA  LGRKINSWES  SRSGHSFLSN  LHLRNGELVI

HEKGFYYIYS  QTYFRFQEEI  KENTKNDKQM  VQYIYKYTSY

PDPILLMKSA  RNSCWSKDAE  YGLYSIYQGG  IFELKENDRI

FVSVTNEHLI  DMDHEASFFG  AFLVG
```

In another embodiment, the PD-L2/TRAIL fusion protein comprises the fusion protein having the amino acid sequence SEQ ID NO: 7. The underlined and bolded amino acids correspond to the second domain, which comprises a portion of TRAIL protein. The bolded amino acids that are not underlined correspond to a linker.

```
                                            (SEQ ID NO: 7)
MIFLLLMLSL  ELQLHQIAAL  FTVTVPKELY  IIEHGSNVTL

ECNFDTGSHV  NLGAITASLQ  KVENDTSPHR  ERATLLEEQL

PLGKASFHIP  QVQVRDEGQY  QCIIIYGVAW  DYKYLTLKVK

ASYRKINTHI  LKVPETDEVE  LTCQATGYPL  AEVSWPNVSV

PANTSHSRTP  EGLYQVTSVL  RLKPPPGRNF  SCVFWNTHVR

ELTLASIDLQ  SQMEPRTHPT  GDPLVTAASV  LEFGGSGGGS

EGGGSEGGGS  EGGGSDIETI  STVQEKQQNI  SPLVRERGPQ

RVAAHITGTR  GRSNTLSSPN  SKNEKALGRK  INSWESSRSG

HSFLSNLHLR  NGELVIHEKG  FYYIYSQTYF  RFQEEIKENT

KNDKQMVQYI  YKYTSYPDPI  LLMKSARNSC  WSKDAEYGLY

SIYQGGIFEL  KENDRIFVSV  TNEHLIDMDH  EASFFGAFLV

G
```

In another embodiment, the PD-L2/TRAIL fusion protein comprises the fusion protein having the amino acid sequence SEQ ID NO: 8. The underlined and bolded amino acids correspond to the second domain, which comprises a portion of TRAIL protein. The bolded amino acids that are not underlined correspond to a linker.

```
                                            (SEQ ID NO: 8)
MIFLLLMLSL  ELQLHQIAAL  FTVTVPKELY  IIEHGSNVTL

ECNFDTGSHV  NLGAITASLQ  KVENDTSPHR  ERATLLEEQL

PLGKASFHIP  QVQVRDEGQY  QCIIIYGVAW  DYKYLTLKVK

ASYRKINTHI  LKVPETDEVE  LTCQATGYPL  AEVSWPNVSV

PANTSHSRTP  EGLYQVTSVL  RLKPPPGRNF  SCVFWNTHVR

ELTLASIDLQ  SQMEPRTHPT  GDPLVTAASV  LEFGGSGGGS

EGGGSEGGGS  EGGGSDIRGP  QRVAAHITGT  RGRSNTLSSP

NSKNEKALGR  KINSWESSRS  GHSFLSNLHL  RNGELVIHEK

GFYYIYSQTY  FRFQEEIKEN  TKNDKQMVQY  IYKYTSYPDP

ILLMKSARNS  CWSKDAEYGL  YSIYQGGIFE  LKENDRIFVS

VTNEHLIDMD  HEASFFGAFL  VG
```

The fusion proteins identified by the SEQ ID NOs listed above include original signal peptides; these signal peptides can be varied according to the needs of the user, the expression system, and other factors, as would be understood by one skilled in the art. Signal peptides are well known in the art, and any desired signal peptide can be used, including those recognized/predicted by publicly available signal peptide recognition software known to those skilled in the art.

In additional embodiments, the PD-L1/TRAIL fusion protein comprises a variant and/or derivative of the amino acid sequence shown in SEQ ID NO: 1, SEQ ID NO: 2, SEQ ID NO: 3 or SEQ ID NO: 4. In further embodiments, the PD-L2/TRAIL fusion protein comprises a variant and/or derivative of the amino acid sequence shown in SEQ ID NO: 5, SEQ ID NO: 6, SEQ ID NO: 7 or SEQ ID NO: 8.

Other suitable second domains in the context of the PD-1 and Fas signaling axis include, for example, the FasL protein itself, variants or derivatives of the FasL protein, or other polypeptides or proteins that are specifically designed to inhibit activation of T cells or other cells and/or induce apoptosis through binding to and triggering the Fas receptor, such as agonistic anti-Fas Ab, and variants and/or derivatives of these. Preferably, the second domain of the fusion protein in this embodiment comprises at least a portion of the extracellular domain of the FasL protein, specifically that portion which is necessary for binding to a Fas receptor. Variants of the wild-type form of the extracellular domain of the FasL protein, or the portion of the extracellular domain responsible for Fas receptor binding and triggering, are also included in the present invention, so long as the variant provides a similar level of biological activity as the wild-type protein.

Accordingly, the term "polypeptide that binds to a Fas receptor" as used herein includes, for example, the FasL protein; the extracellular domain of the FasL protein; a polypeptide which comprises at least a portion of the extracellular domain of the FasL protein, which portion is responsible for binding to a Fas receptor; antibodies to a Fas receptor; lipocalins engineered to bind to a Fas receptor; and variants and/or derivatives of any of these. The term "FasL" is understood to embrace polypeptides corresponding to the complete amino acid sequence of the FasL protein, including the cytoplasmic, transmembrane and extracellular domains, as well as polypeptides corresponding to smaller portions of the protein, such as the extracellular domain, or a portion of the extracellular domain. In one embodiment the second domain of the PD-L1/FasL or PD-L2/FasL signaling pair comprises at least a portion of the extracellular domain of the human FasL protein.

In one embodiment, the fusion protein is a PD-L1/FasL fusion protein. In an embodiment, the PD-L1/FasL fusion protein comprises the fusion protein having the amino acid sequence SEQ ID NO:9. The underlined and bolded amino acids correspond to the second domain, which comprises a portion of FasL protein.

```
                                               (SEQ ID NO: 9)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVILEKQ IGHPSPPPEK

KELRKVAHLT GKSNSRSMPL EWEDTYGIVL LSGVKYKKGG

LVINETGLYF VYSKVYFRGQ SCNNLPLSHK VYMRNSKYPQ

DLVMMEGKMM SYCTTGQMWA RSSYLGAVFN LTSADHLYVN

VSELSLVNFE ESQTFFGLYK L
```

In an embodiment, the PD-L1/FasL fusion protein comprises the fusion protein having the amino acid sequence SEQ ID NO: 10. The underlined and bolded amino acids correspond to the second domain which is a portion of TRAIL protein. The bolded amino acids that are not underlined correspond to the linker.

```
                                              (SEQ ID NO: 10)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIGDPL VTAASVLEFG

GSGGGSEGGG SEGGGSEGGG SDILEKQIGH PSPPPEKKEL

RKVAHLTGKS NSRSMPLEWE DTYGIVLLSG VKYKKGGLVI

NETGLYFVYS KVYFRGQSCN NLPLSHKVYM RNSKYPQDLV

MMEGKMMSYC TTGQMWARSS YLGAVFNLTS ADHLYVNVSE

LSLVNFEESQ TFFGLYKL
```

In another embodiment, the fusion protein comprises a PD-L2/FasL fusion protein. In an embodiment, the PD-L2/FasL fusion protein comprises a fusion protein having the amino acid sequence SEQ ID NO:11. The underlined and bolded amino acids correspond to the second domain, which comprises a portion of FasL protein.

```
                                              (SEQ ID NO: 11)
MIFLLLMLSL ELQLHQIAAL FTVTVPKELY IIEHGSNVTL

ECNFDTGSHV NLGAITASLQ KVENDTSPHR ERATLLEEQL

PLGKASFHIP QVQVRDEGQY QCIIIYGVAW DYKYLTLKVK

ASYRKINTHI LKVPETDEVE LTCQATGYPL AEVSWPNVSV

PANTSHSRTP EGLYQVTSVL RLKPPPGRNF SCVFWNTHVR

ELTLASIDLQ SQMEPRTHPT LEKQIGHPSP PPEKKELRKV

AHLTGKSNSR SMPLEWEDTY GIVLLSGVKY KKGGLVINET

GLYFVYSKVY FRGQSCNNLP LSHKVYMRNS KYPQDLVMME

GKMMSYCTTG QMWARSSYLG AVFNLTSADH LYVNVSELSL

VNFEESQTFF GLYKL
```

In another embodiment, the PD-L2/FasL fusion protein comprises the fusion protein having the amino acid sequence SEQ ID NO: 12. The underlined and bolded amino acids correspond to the second domain, which comprises a portion of FasL protein. The bolded amino acids that are not underlined correspond to a linker.

```
                                              (SEQ ID NO: 12)
MIFLLLMLSL ELQLHQIAAL FTVTVPKELY IIEHGSNVTL

ECNFDTGSHV NLGAITASLQ KVENDTSPHR ERATLLEEQL

PLGKASFHIP QVQVRDEGQY QCIIIYGVAW DYKYLTLKVK

ASYRKINTHI LKVPETDEVE LTCQATGYPL AEVSWPNVSV

PANTSHSRTP EGLYQVTSVL RLKPPPGRNF SCVFWNTHVR

ELTLASIDLQ SQMEPRTHPT GDPLVTAASV LEFGGSGGGS

EGGGSEGGGS EGGGSDILEK QIGHPSPPPE KKELRKVAHL

TGKSNSRSMP LEWEDTYGIV LLSGVKYKKG GLVINETGLY

FVYSKVYFRG QSCNNLPLSH KVYMRNSKYP QDLVMMEGKM

MSYCTTGQMW ARSSYLGAVF NLTSADHLYV NVSELSLVNF

EESQTFFGLY KL
```

SEQ ID NOs 9-12 include signal peptides; these signal peptides can be varied according to the needs of the user, the expression system, and other factors, as would be understood by one skilled in the art. Signal peptides are well known in the art, and any desired signal peptide can be used, including those recognized/predicted by publicly available signal peptide recognition software known to those skilled in the art.

In additional embodiments, the PD-L1/FasL fusion protein comprises a variant and/or derivative of the amino acid sequence shown in SEQ ID NO:9 or SEQ ID NO:10. In further embodiments, the PD-L2/FasL fusion protein is a variant and/or derivative of the amino acid sequence shown in SEQ ID NO:11 or SEQ ID NO:12.

In one embodiment, it is believed that the fusion proteins of the present invention inhibit activation of the immune system by preventing or reducing proliferation and differentiation of myelin-specific T cells, or by inducing apoptosis those cells. In some embodiments the fusion proteins of the present invention may inhibit production of pro-inflammatory cytokines and chemokines, such as IL-6, IL-8, RANTES, IP-10, and MCP-1, or inhibit potentiation of other cytokines/chemokines, such as TNF-α, and IL-1β; or inhibit induction of matrix metalloproteinases such as MMP-1 and MMP-9; or inhibit prostaglandin E2 secretion from fibroblasts and synoviocytes. The present invention embraces inhibition/down-regulation of any and all cytokines that are either promoted by PD-L1 or PD-L2 or down-modulated by the TRAIL ligand.

In other embodiments the fusion proteins of the present invention inhibit autoreactive T cell proliferation, autoreactive antibody production, and inflammatory reactions. In some embodiments, the fusion proteins of the present invention induce apoptosis in autoreactive T cells.

In additional embodiments, the fusion proteins of the present invention are believed to reduce inflammation as may be determined (i) in in vitro and in vivo assays that measure inhibition of pro-inflammatory cytokine and chemokine production and/or elevation of anti-inflammatory cytokine production; or (ii) in in vivo model systems of inflammation, such as autoimmune disease models, for example, EAE and collagen-induced arthritis, and delayed-type hypersensitivity and other models in which pro-inflammatory agents are introduced locally or systemically into animals. In these in vivo models, inflammation is assessed by histological examination of inflamed tissues, isolation of inflammatory cells from diseased tissues, and measurement of disease manifestations in affected animals. The fusion proteins of the present invention, in other embodiments, are believed to inhibit the proliferation, differentiation and/or effector function of pathogenic T cells such as autoreactive CD4+ T cells and CD8+ T cells and other pathogenic immune cells such as B cells, natural (NK) cells, NKT cells, lymphoid progenitor cells, dendritic cells, monocytes/macrophages; induce apoptosis in pathogenic immune cells; promote generation of immune cells with regulatory properties (such as CD4+CD25+ regulatory T cells, Tr1 cells, CD8+, NK NKT, and dendritic cells with immuno-inhibitory activities); decrease permeability of the blood-brain barrier, and thereby restrict access of inflammatory cells to the CNS; decrease access of inflammatory cells to other disease sites, and decrease angiogenesis associated with inflammation.

Most (although not all) of the TNF receptor (TNFR) superfamily members are type II transmembrane proteins. These proteins contain an extracellular domain that is structurally characterized by the presence of one to six cysteine-rich domains (CRDs). The typical CRD is approximately 40 amino acids in length and contains six conserved cysteine residues that form three intrachain disulphide bridges. The CRD itself is typically composed of two distinct structural modules.

TRAIL

TRAIL is a Type II membrane protein having 281 amino acids and has been sequenced in a number of species, including, but not limited to, mouse: Swiss Prot. Accession No. P50592: human: Swiss Prot. Accession No. P50591; *Rattus norvegicus*: NCBI Accession NP-663714; Siniperca Chuatsi (Chinese Perch): NCBI Accession AAX77404; *Gallus Gallus* (Chicken): NCBI Accession BAC79267; *Sus Scrofa* (Pig): NCBI Accession NP-001019867; *Ctenopharyngodon Idella* (Grass Carp): NCBI Accession AAW22593; and *Bos Taurus* (Cattle): NCBI Accession XP-001250249.

The extracellular domain of TRAIL comprises amino acids 39-281, and the TNF domain responsible for receptor binding comprises amino acids 121-280, based on TNF homology models. The portion of the protein that is particularly important for conferring activity has been identified. See, e.g., "Triggering cell death: The crystal structure of Apo2L/TRAIL in a complex with death receptor", Hymowitz S G, et al., Am. Mol. Cell. 1999 October; 4(4):563-71), incorporated herein by reference, which reports the most important amino acids for TRAIL binding to its receptor and activity are amino acids around the zinc area such as amino acids (191-201-205-207-236-237) and amino acids (150-216). See also, (1) Krieg A et al 2003 Br. J of Cancer 88: 918-927, which describes two human TRAIL variants without apoptotic activity, TRAIL-γ and TRAIL β; (2) "Enforced covalent trimerization increases the activity of the TNF ligand family members TRAIL and CD95L", D Berg et al., Cell death and differentiation (2007)14, 2021-2034; and (3) "Crystal Structure of TRAIL-DR5 complex identifies a critical role of the unique frame insertion in conferring recognition specificity", S. Cha et al., J. Biol. Chem. 275: 31171-31177 (2000), all incorporated herein by reference.

TRAIL is known to ligate two types of receptors: death receptors triggering TRAIL-induced apoptosis and decoy receptors that possibly inhibit this pathway. Four human receptors for TRAIL have been identified: TRAILR1, TRAILR2, TRAILR3 and TRAILR4. TRAILR1 and TRAILR2 when triggered induce apoptosis. However, TRAILR3 and TRAILR4 are decoy receptors that do not induce apoptosis. TRAIL can also bind to osteoprotegrin (OPG). Binding to each of these receptors has been well-characterized, e.g., "The TRAIL apoptotic pathway in cancer onset, progression and therapy," *Nature Reviews Cancer* Volume 8 (2008) 782-798.

Full-length human TRAIL (UniProtKG/Swiss-Prot accession number P50591.1) has the following amino acid sequence (SEQ ID NO:13). The extracellular domain comprising amino acids 38-281 is underlined and in bold:

(SEQ ID NO: 13)
MAMMEVQGGP SLGQTCVLIV IFTVLLQSLC VAVTYVYFTN

ELKQMQDKYS KSGIACFLKE DDSYWDPNDE ESMNSPCWQV

KWQLRQLVRK MILRTSEETI STVQEKQQNI SPLVRERGPQ

RVAAHITGTR GRSNTLSSPN SKNEKALGRK INSWESSRSG

HSFLSNLHLR NGELVIHEKG FYYIYSQTYF RFQEEIKENT

KNDKQMVQYI YKYTSYPDPI LLMKSARNSC WSKDAEYGLY

SIYQGGIFEL KENDRIFVSV TNEHLIDMDH EASFFGAFLV

G

In some preferred embodiments, the second domain of the fusion protein comprises the following amino acid sequence (SEQ ID NO:14) from human TRAIL:

(SEQ ID NO: 14)
ETI STVQEKQQNI SPLVRERGPQ

RVAAHITGTR GRSNTLSSPN SKNEKALGRK INSWESSRSG

HSFLSNLHLR NGELVIHEKG FYYIYSQTYF RFQEEIKENT

KNDKQMVQYI YKYTSYPDPI LLMKSARNSC WSKDAEYGLY

SIYQGGIFEL KENDRIFVSV TNEHLIDMDH EASFFGAFLV

G

In some preferred embodiments, the second domain of the fusion protein comprises the following amino acid sequence (SEQ ID NO:15) from human TRAIL:

(SEQ ID NO: 15)
RGPQ

RVAAHITGTR GRSNTLSSPN SKNEKALGRK INSWESSRSG

HSFLSNLHLR NGELVIHEKG FYYIYSQTYF RFQEEIKENT

KNDKQMVQYI YKYTSYPDPI LLMKSARNSC WSKDAEYGLY

SIYQGGIFEL KENDRIFVSV TNEHLIDMDH EASFFGAFLV

G

In some embodiments, the second domain of the fusion protein of the invention comprises the extracellular domain of the human TRAIL protein. In other embodiments, the second domain of the fusion protein comprises a fragment of TRAIL comprising at least 20, 30, 40, 50, 60, 70, 80, 90, 100, 110, 120, 130, 140, 150, 160, 170, 180, 190, 200, 210, 220, 230, 240, 250, 260, 270 or 280 contiguous amino acids of the full-length TRAIL protein, wherein the fragment binds and triggers TRAIL receptor.

Fas Ligand

Fas ligand (FasL) is a cytokine that binds to TNFRSF6/FAS, a receptor that transduces the apoptotic signal into cells. It may be involved in cytotoxic T-cell mediated apoptosis and in T-cell development. Fas-mediated apoptosis may have a role in the induction of peripheral tolerance, in the antigen-stimulated suicide of mature T cells, or both. Fas ligand has been sequenced in several species including human (UniProtKB/Swiss-Prot accession number P48023), mouse (GenBank accession number AAA19778.1), horse (GenBank accession number ACV52391.1), cat (GenBank accession number BAC76426.1) and cattle (GenBank accession number AEV59556.1).

The extracellular domain of Fas ligand comprises Fas ligand amino acids 103-281. The cytoplasmic domain comprises amino acids 1-80, and the transmembrane domain comprises amino acids 81-102.

The amino acid sequence of full-length human Fas ligand (FASLG; CD95L; FASL; TNFSF6) protein is shown below (SEQ ID NO:16) (UniProtKB/Swiss-Prot accession number P48023). The extracellular domain, comprising amino acids 103-281, is underlined and in bold:

(SEQ ID NO: 16)
MQQPFNYPYP QIYWVDSSAS SPWAPPGTVL PCPTSVPRRP

GQRRPPPPPP PPPLPPPPPP PPLPPLPLPP LKKRGNHSTG

LCLLVMFFMV LVALVGLGLG MFQLFHLQKE LAELRESTSQ

MHTASSLEKQ IGHPSPPPEK KELRKVAHLT GKSNSRSMPL

EWEDTYGIVL LSGVKYKKGG LVINETGLYF VYSKVYFRGQ

SCNNLPLSHK VYMRNSKYPQ DLVMMEGKMM SYCTTGQMWA

RSSYLGAVFN LTSADHLYVN VSELSLVNFE ESQTFFGLYK

L

In some preferred embodiments, the second domain of the fusion protein comprises the following amino acid sequence (SEQ ID NO:17) from human FasL:

(SEQ ID NO: 17)
LEKQIGHPSPPPEK KELRKVAHLT GKSNSRSMPL

EWEDTYGIVL LSGVKYKKGG LVINETGLYF VYSKVYFRGQ

SCNNLPLSHK VYMRNSKYPQ DLVMMEGKMM SYCTTGQMWA

RSSYLGAVFN LTSADHLYVN VSELSLVNFE ESQTFFGLYK

L

In some embodiments, the second domain of the fusion protein of the invention comprises the extracellular domain of the human FasL protein. In other embodiments, the second domain of the fusion protein comprises a fragment of FasL protein comprising at least 20, 30, 40, 50, 60, 70, 80, 90, 100, 110, 120, 130, 140, 150, 160, 170, 180, 190, 200, 210, 220, 230, 240, 250, 260, 270 or 280 contiguous amino acids of the full-length FasL protein, wherein fragment binds to and triggers Fas receptor.

PD-L1 and PD-L2

The signal peptide of PD-L1 comprises amino acids 1-17 or 1-18, depending on the source. The extracellular binding domain of PD-L1 comprises amino acids 18-239 or 19-239, depending on the source.

The amino acid sequence of full-length human PD-L1 (B7-H1; PDCD1L1; PDL1; CD274) protein is shown below (SEQ ID NO:18) (UniProtKB/Swiss-Prot accession number Q9NZQ7.1). The extracellular domain, comprising amino acids 18-239 or 19-239, depending on the source, is underlined and in bold:

(SEQ ID NO: 18)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIPELP LAHPPNERTH

LVILGAILLC LGVALTFIFR LRKGRMMDVK KCGIQDTNSK

KQSDTHLEET

In some embodiments, the first domain of the fusion protein of the invention comprises the extracellular domain of the human PD-L1 protein. In other embodiments, the first domain of the fusion protein comprises a fragment of PD-L1 comprising at least 20, 30, 40, 50, 60, 70, 80, 90, 100, 110, 120, 130, 140, 150, 160, 170, 180, 190, 200, 210, 220, 230, 240, 250, 260, 270 or 280 contiguous amino acids of the full-length PD-L1 protein, wherein the fragment binds to and triggers PD-1.

The signal peptide of PD-L2 comprises amino acids 1-18 or 1-19, depending on the source. The extracellular domain of PD-L2 comprises amino acids 20-220.

The amino acid sequence of full-length human PD-L2 (B7-DC; PDCD1L2; PDL2) protein is shown below (UniProtKB/Swiss-Prot accession number Q9BQ51) (SEQ ID NO:19). The extracellular domain, comprising amino acids 20-220, is underlined and in bold:

(SEQ ID NO: 19)
MIFLLLMLSL ELQLHQIAAL FTVTVPKELY IIEHGSNVTL

ECNFDTGSHV NLGAITASLQ KVENDTSPHR ERATLLEEQL

PLGKASFHIP QVQVRDEGQY QCIIIYGVAW DYKYLTLKVK

-continued

```
ASYRKINTHI LKVPETDEVE LTCQATGYPL AEVSWPNVSV

PANTSHSRTP EGLYQVTSVL RLKPPPGRNF SCVFWNTHVR

ELTLASIDLQ SQMEPRTHPT WLLHIFIPFCIIAFIFIATV

IALRKQLCQK LYSSKDTTKR PVTTTKREVN SAI
```

In the following PD-L1 amino acid sequence (SEQ ID NO:18), the IgV-like domain is underlined and IgC-like domain is double underlined.

```
                                     (SEQ ID NO: 18)
MRIFAVFIFM TYWHLLNAFT VTVPKDLYVV EYGSNMTIEC

KFPVEKQLDL AALIVYWEME DKNIIQFVHG EEDLKVQHSS

YRQRARLLK DQLSLGNAAL QITDVKLQDA GVYRCMISYG

GADYKRITVK VNAPYNKINQ RILVVDPVTS EHELTCQAEG

YPKAEVIWTS SDHQVLSGKT TTTNSKREEK LFNVTSTLRI

NTTTNEIFYC TFRRLDPEEN HTAELVIPEL PLAHPPNERT

HLVILGAILL CLGVALTFIF RLRKGRMMD VKKCGIQDT

NSKKQSDTH LEET
```

In the following PD-L2 amino acid sequence (SEQ ID NO:19), the IgV-like domain is underlined and IgC-like domain is double underlined.

```
                                     (SEQ ID NO: 19)
MIFLLLMLSL ELQLHQIAAL FTVTVPKELY IIEHGSNVTL

ECNFDTGSHV NLGAITASLQ KVENDTSPHR ERATLLEEQL

PLGKASFHIP QVQVRDEGQY QCIIIYGVAW DYKYLTLKVK

ASYRKINTHI LKVPETDEVE LTCQATGYPL AEVSWPNVSV

PANTSHSRTP EGLYQVTSVL RLKPPPGRNF SCVFWNTHVR

ELTLASIDLQ SQMEPRTHPT WLLHIFIPFC IIAFIFIATV

IALRKQLCQK LYSSKDTTKR PVTTTKREVN SAI
```

In some embodiments, the first domain of the fusion protein of the invention comprises the extracellular domain of the PD-L2 protein. In other embodiments, the first domain of the fusion protein comprises a fragment of PD-L2 comprising at least 20, 30, 40, 50, 60, 70, 80, 90, 100, 110, 120, 130, 140, 150, 160, 170, 180, 190, 200, 210, 220, 230, 240, 250, 260, 270 or 280 contiguous amino acids of the full-length PD-L2 protein, wherein the fragment binds to and triggers PD-1.

Linkers

The first and second domains of the fusion proteins of the invention may be optionally connected via a linker. The residues for the linker may be selected from naturally occurring amino acids, non-naturally occurring amino acids, and modified amino acids. The linker will typically connect the carboxy terminus of the first domain to the amino terminus of the second domain. The reverse is also possible, i.e., using the linker to connect the carboxy terminus of the second domain to the amino terminus of the first domain. The linker may alter the distance between the two structural components of the fusion protein, as well as alter the flexibility of this region. The linker may comprise any number of amino acids. The linker may thus comprise, for example, 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids. In some embodiments, the linker may be composed of from 3 to 60 amino acid residues, from 3 to 40 amino acids, from 3 to 30 amino acids, from 3 to 24 amino acids, from 3 to 18 amino acids, or from 3 to 15 amino acids. The linker may comprise, for example, a repeating sub-sequence of 2, 3, 4, 5 or more amino acid residues, comprising 2, 3, 4, 5, 6, 7, 8, 9, 10, 11, 12 or more repeats of the sub-sequence.

Linkers may be naturally-occurring sequences or designed sequences. Peptide linkers useful in the molecule of the invention include, but are not limited to, glycine linkers, glycine-rich linkers, serine-glycine linkers, and the like. A glycine-rich linker comprises at least about 50% glycine and preferably at least about 60% glycine. In one embodiment, the linker comprises the amino acid sequence Gly-Ser, or repeats thereof. See, e.g., Huston, et al., *Methods in Enzymology*, 203:46-88 (1991). In another embodiment, the linker comprises the amino acid sequence Glu-Lys, or repeats thereof. See, e.g., Whitlow et al., *Protein Eng.*, 6:989 (1993)). In another embodiment, the linker comprises the amino acid sequence Gly-Gly-Ser, or repeats thereof. In another embodiment, the linker comprises the amino acid sequence Gly-Gly-Gly-Gly-Ser (SEQ ID NO:20), or repeats thereof. In certain specific embodiments, the linker contains from 2 to 12 repeats of Gly-Gly-Ser or Gly-Gly-Gly-Gly-Ser (SEQ ID NO:21). See U.S. Pat. No. 6,541,219 for examples of peptide linkers. In another embodiment, the linker comprises the amino acid sequence of SEQ ID NO: 22: GDPLVTAASVLEF-GGSGGGSEGGGSEGGGSEGGGSDI.

Linkers comprising human immunoglobulin Fc region sequences are also useful. An exemplary Fc region linker includes but is not limited to: the hinge region of human IgG1 (EPKSCDKTHTCPPCP; SEQ ID NO:23); the $C_{H2}$ and $C_{H3}$ domains of a human IgG1; and a second IgG1 hinge region. An exemplary sequence for this linker comprises (SEQ ID NO: 24). The hinge region sequences are underlined.

```
                                     (SEQ ID NO: 24)
EPKSCDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GKEPKSCDKT

HTCPPCP
```

In another embodiment, the hinge region and the $C_{H2}$ and $C_{H3}$ domains of human IgG1 are mutated to prevent inter-chain disulfide bonds, to reduce antibody dependent cellular cytotoxicity (ADCC), or to eliminate N-linked glycosylation (aglycosyl human IgG1). An exemplary sequence for this linker comprises the sequence below, wherein mutated sequences are in bold and underlined.

```
                                     (SEQ ID NO: 25)
EPKSSDKTHT SPPSPAPPVA GAPSVFLFPP KPKDTLMISR

TPEVTCVVVD VSHEDPEVKF NWYVDGVEVH NAKTKPREEQ

YASTYRVVSV LTVLHQDWLN GKEYKCKVSN KALPAPIEKT
```

-continued

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GK

Linkers are useful for separating the two components of the fusion protein to enable proper folding of the components, to reduce potential steric problems, and/or to contribute optimal receptor binding. The skilled artisan is familiar with the design and selection of peptide linkers. See, for instance, Robinson et al., 1998, *Proc. Natl. Acad. Sci. USA* 95:5929-5934. Automated programs are also available for peptide linker design (e.g., Crasto et al., 2000, *Protein Engineering* 13:309-312).

Optional Other Elements

The fusion protein optionally may also include further elements apart from the first domain, the second domain and the optional linker. Such further elements may include: an initiator methionine, a signal peptide, a trimerization domain, an antigen polypeptide, and a purification tag, such as His-6. Fusion proteins essentially consisting of the first domain and the second domain and an optional linker are preferred embodiments in the context of the present invention.

Fusion proteins of the invention optionally comprise a signal peptide. Signal peptides can be varied according to the needs of the user, the expression system, and other factors, as would be understood by one skilled in the art. Signal peptides are well known in the art, and any desired signal peptide can be used, including those recognized/predicted by publicly available signal peptide recognition software known to those skilled in the art.

TRAIL and FasL both require trimerization for optimal receptor binding. Naturally-occurring TRAIL and FasL each can form trimers, however, the trimers can be unstable. Thus, addition of a heterologous trimerization domain to TRAIL and FasL may further increase receptor binding affinity by increasing the likelihood of formation and stabilization of the resulting protein. Thus, in an embodiment, the fusion protein of the invention optionally further comprises a heterologous trimerization domain. Within the fusion protein, the heterologous trimerization domain may be positioned anywhere within the fusion protein, provided it does not disrupt the functional activity of the fusion protein, e.g., binding to and triggering PD-1 and TRAIL receptor or Fas receptor. For instance, the trimerization domain should not disrupt the IgSF domain of PD-L1 or PD-L2 that underlies binding to PD-1. Similarly, the heterologous trimerization domain should not disrupt the binding and triggering function of the TRAIL or FasL domain. The heterologous trimerization domain may be positioned within the first domain outside of its IgSF domains, or between the first domain and the optional linker, or within or in place of the optional linker, or between the optional linker and the second domain, or at the C-terminal terminus of the fusion protein. It is preferable that the heterologous trimerization domain is positioned substantially adjacent to the second domain, to optimize the formation of the second domain trimers. In a preferred embodiment, however, the trimerization domain is not positioned at the C-terminal terminus of the fusion protein.

Trimerization domains are well known in the art. Non-limiting examples of trimerization domains suitable as a heterologous trimerization domain in the fusion protein of the invention include: the GCN4 leucine zipper (Harbury et al., 1993, "A switch between two-, three-, and four-stranded coiled coils in GCN4 leucine zipper mutants," *Science* 262(5138):1401-7); a 35 amino-acid sequence from lung surfactant protein (Hoppe et al., 1994, "A parallel three stranded alpha-helical bundle at the nucleation site of collagen triple-helix formation," *FEBS Lett.* 344(2-3):191-5); short, repeating heptad sequences from collagen (McAlinden et al., 2003, "Alpha-helical coiled-coil oligomerization domains are almost ubiquitous in the collagen superfamily," *J. Biol Chem.* 278(43):42200-7. Epub 2003 Aug. 14.); and the bacteriophage T4 fibritin "foldon" (see, e.g., Miroshnikov et al., 1998, "Engineering trimeric fibrous proteins based on bacteriophage T4 adhesins," *Protein Eng.* 11(4): 329-32). Exemplary trimerization domains are also disclosed in U.S. Pat. Nos. 6,911,205 and 8,147,843, and U.S. Pat. Appln. Pub. 2010/0136032. An exemplary trimerization sequence is the T4 "foldon" having the sequence: GYIPEAPRDGQAYVRKRGEWVLLSTFL (SEQ ID NO: 26). Another exemplary trimerization domain is from thrombospondin-1 and has the sequence: VTTLQDSIRKVTEENKELANELRR (SEQ ID NO: 27).

Modifications

Additional modifications can be introduced such as those that further stabilize the TRAIL trimer and/or increase affinity of binding to the TRAIL receptor, or stabilize the Fas L trimer and/or increase affinity of binding to Fas receptor; and spacers/linkers can be added to alter the distance between the two structural components of the fusion protein, as well as alter the flexibility of this region.

In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilised metals (Porath J (1992) Protein Expr Purif 3-26328 1), protein A domains that allow purification on immobilised immunoglobulin, and the domain utilised in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and the fusion proteins of the present invention is useful to facilitate purification.

This invention relates to PD-L1/TRAIL, PD-L2/TRAIL, PD-L1/FasL, PD-L2/FasL and related fusion proteins. The invention also encompasses variants of the fusion proteins. While in general it is desirable for variants to show enhanced ability for binding to a given molecule, in some embodiments variants may be designed with slightly reduced activity as compared to other fusion proteins of the invention, for example, in instances in which one would purposefully want to attenuate activity. Moreover, variants or derivatives can be generated that would bind more selectively to one of the TRAIL receptor variants (there are three TRAIL receptors in humans). Furthermore, variants or derivatives can be generated that would have altered multimerization properties. When engineering variants, this could be done for either the entire TRAIL extracellular domain, or for that component of the extracellular domain that is incorporated within the fusion protein itself.

Preferably, variants or derivatives of the fusion proteins of the present invention maintain the hydrophobicity/hydrophilicity of the amino acid sequence.

The invention also provides chemical modification of a fusion protein of the invention. Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a fusion protein conjugated with polyethylene glycol (PEG), or addition of PEG during chemical synthesis of a polypeptide of the invention. Modifications of polypeptides or portions thereof can also include reduction/alkylation; chemical coupling to an appropriate carrier or mild formalin treatment.

Other derivatives of the fusion proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylation site(s) are added or glycosylation sites are deleted or disabled. Furthermore, if no glycosylation is desired, the proteins can be produced in a prokaryotic host expression system.

Variants and/or derivatives of the fusion proteins of the invention can be prepared by chemical synthesis or by using site-directed mutagenesis (Gillman et al., *Gene* 8:81 (1979); Roberts et al., *Nature* 328:731 (1987) or Innis (Ed.), 1990, *PCR Protocols: A Guide to Methods and Applications*, Academic Press, New York, N.Y.) or the polymerase chain reaction method (PCR; Saiki et al., Science 239:487 (1988)), as exemplified by Daugherty et al. (Nucleic Acids Res. 19:2471 (1991)) to modify nucleic acids encoding the complete receptors.

Additional modifications can be introduced such as those that further stabilize the TRAIL trimer and/or increase affinity of binding to the TRAIL receptor. In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath J (1992) Protein Expr Purif 3-0.26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and PD-L1/TRAIL, PD-L2/TRAIL, PD-L1/FasL or PD-L2/FasL is useful to facilitate purification.

PD-L1 and PD-L2 are monomeric. However, once linked to second domain components TRAIL or FasL which are naturally trimeric, a de facto PD-L1 or PD-L2 trimer is formed. This serves to bring PD-1 receptors into proximity, likely enhancing their triggering. Additionally, higher-order complexes may result, such as hexamers, which are formed for example in the case of FasL when engaged with its receptor Fas.

In another embodiment a fusion protein of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products).

In order to enhance stability and/or reactivity, the fusion proteins of the present invention can also be modified to incorporate one or more polymorphisms in the amino acid sequence resulting from natural allelic variation. Additionally, D-amino acids, non-natural amino acids or non-amino acid analogues can be substituted or added to produce a modified fusion protein within the scope of this invention.

Expression of Fusion Proteins

The amino acid sequences of the present invention may be produced by expression of a nucleotide sequence coding for same in a suitable expression system.

Fusion protein expression vectors include pGEX (Pharmaci, a Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used. In addition, retroviral and lentiviral expression vectors can also be used. Furthermore, any one of a number of in vivo expression systems designed for high level expression of recombinant proteins within organisms can be invoked for producing the fusion proteins specified herein.

In addition, or in the alternative, the fusion protein itself can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) *Proteins Structures And Molecular Principles*, WH Freeman and Co, New York N.Y.). The composition of the synthetic polypeptides may be confirmed by amino acid analysis or sequencing (e.g., the Edman degradation procedure). Additionally, the amino acid sequence of a fusion protein of the invention, or any part thereof, may be altered during direct synthesis and/or combined using chemical methods with a sequence from other subunits, or any part thereof, to produce a variant polypeptide.

Assays for Fusion Protein Activity

Any of the various immunologic assays known in the art may be used to measure the immunologic activity of any fusion protein.

For example, any one of several conventional assays for monitoring cytokine production, as a measure of immune cells activation and differentiation, can be invoked. For example, for tracking T cell activation, interleukin-2 can be employed as a marker, which can be assayed as described in Thompson C B, et al., Proc. Natl. Acad. Sci. USA. 86:1333 (1989) the entire disclosure of which is incorporated herein by reference. A kit for an assay for the production of interferon is also available from Genzyme Corporation (Cambridge, Mass.). One can also employ immunofluorescence and flow cytometry to monitor cytokine production on a cellular basis, and to monitor cell surface markers that reflect cellular activation and/or differentiation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of 3H-labeled thymidine incorporated into the replicating DNA of cultured cells. Therefore, the rate of DNA synthesis and, in turn, the rate of cell division can be quantified.

Another assay for monitoring T cell proliferation is based on loading T cells with the CFSE dye, and subsequently monitoring by flow cytometry the dilution of this dye that accompanies successive cell divisions. In addition to monitoring the inhibition of T cell proliferation, the bioactivity of the fusion protein can also be monitored by evaluating its capacity to induce apoptosis in TRAIL receptor-positive tumor cell lines in which TRAIL receptor triggering leads to apoptosis. By combining these cells with other cells that have PD-1 on their surfaces, one can assess whether new fusion protein derivatives both anchor to PD-1 and thereby have their pro-apoptotic TRAIL-driven activity enhanced in this way.

Pharmaceutical Compositions, Dosing Regimens and Treatment Methods

Administration of the compositions of this invention is typically parenteral, such as by subcutaneous, intravenous, intramuscular, or intraperitoneal injection, or by infusion or by any other acceptable systemic method. Administration by subcutaneous injection is a preferred embodiment. An alternative route of administration is by intravenous infusion, which may typically take place over a time course of about 1 to 5 hours. In addition, there are a variety of oral delivery methods for administration of therapeutic proteins, and these can be applied to the therapeutic fusion proteins of this invention.

Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg protein per kilogram of body weight. Various modifications or derivatives of the fusion proteins, such as addition of polyethylene glycol chains (PEGylation), may be made to influence their pharmacokinetic and/or pharmacodynamic properties.

To administer the fusion protein by other than parenteral administration, it may be necessary to coat the protein with, or co-administer the protein with, a material to prevent its inactivation. For example, protein may be administered in an incomplete adjuvant, co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) J. Neuroimmunol. 7:27).

The amount of the fusion protein of the invention administered will be an amount that will ameliorate one or more of the well-known parameters that characterize medical conditions caused by autoimmune disease, alloimmune disease, inflammatory disease or cancer. One such autoimmune disease is multiple sclerosis, for example. Many such parameters and conditions have been described. An effective amount, in the context of multiple sclerosis, will be the amount of fusion protein that is sufficient to accomplish one or more of the following: decrease the severity of symptoms; decrease the duration of disease exacerbations; increase the frequency and duration of disease remission/symptom-free periods; prevent fixed impairment and disability; and/or prevent/attenuate chronic progression of the disease. Clinically, this would result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically the treatment with fusion proteins of the present invention is believed to be capable of one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

Although the compositions of this invention can be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. Remington's Pharmaceutical Science, 17th Ed. (Mack Publishing Company, Easton, Pa., 1990). Alternatively, compositions of the invention may be introduced into a patient's body by implantable drug delivery systems (Urquhart et al., Ann. Rev. Pharmacol. Toxicol. 24:199 (1984)).

Therapeutic formulations may be administered in many conventional dosage formulations. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics,* 8th Ed., Pergamon Press; and *Remington's Pharmaceutical Sciences,* supra, Easton, Pa.; Avis et al. (eds.) (1993) *Pharmaceutical Dosage Forms: Parenteral Medications* Dekker, N.Y.; Lieberman et al. (eds.) (1990) *Pharmaceutical Dosage Forms: Tablets* Dekker, N.Y.; and Lieberman et al. (eds.) (1990), *Pharmaceutical Dosage Forms: Disperse Systems* Dekker, N.Y.

In additional embodiments, the present invention contemplates administration of the fusion proteins by gene therapy methods, e.g., administration of an isolated nucleic acid encoding a fusion protein of interest. The protein building blocks (e.g., first and second domains) of the fusion proteins of the present invention have been well-characterized, both as to the nucleic acid sequences encoding the proteins and the resultant amino acid sequences of the proteins. Engineering of such isolated nucleic acids by recombinant DNA methods is well within the ability of one skilled in the art. Codon optimization, for purposes of maximizing recombinant protein yields in particular cell backgrounds, is also well within the ability of one skilled in the art. Administration of an isolated nucleic acid encoding the fusion protein is encompassed by the expression "administering a therapeutically effective amount of a fusion protein". Gene therapy methods are well known in the art. See, e.g., WO96/07321 which discloses the use of gene therapy methods to generate intracellular antibodies. Gene therapy methods have also been successfully demonstrated in human patients. See, e.g., Baumgartner et al., Circulation 97: 12, 1114-1123 (1998), and more recently, Fatham, C. G. 'A gene therapy approach to treatment of autoimmune diseases', Immun. Res. 18:15-26 (2007); and U.S. Pat. No. 7,378,089, both incorporated herein by reference. See also Bainbridge J W B et al. "Effect of gene therapy on visual function in Leber's congenital Amaurosis". N Engl Med 358:2231-2239, 2008; and Maguire A M et al. "Safety and efficacy of gene transfer for Leber's. Congenital Amaurosis". N Engl J Med 358:2240-8, 2008.

There are two major approaches for introducing a nucleic acid encoding the fusion protein (optionally contained in a vector) into a patients cells; in vivo and ex vivo. For in vivo delivery the nucleic acid is injected directly into the patient, usually at the site where the fusion protein is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors such as adenovirus, Herpes simplex I virus, adeno-associated virus; lipid-based systems (useful lipids for lipid-mediated transfer of the gene are DOTMA, DOPE and DC-Chol, for example); naked DNA; and transposon-based expression systems. For a review of gene marking and gene therapy protocols, see Anderson et al., Science 256:808-813 (1992). See also WO 93/25673 and the references cited therein.

"Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g. by substituting their negatively charged phosphodiester groups by uncharged groups. The fusion proteins of the present invention can be delivered using gene therapy methods, for example locally in tumor beds, intrathecally, or systemically (e.g., via vectors that selectively target specific tissue types, for example, tissue-specific adeno-associated viral vectors). In some embodiments, primary cells (such as lymphocytes or stem cells) from the individual can be transfected ex vivo with a gene encoding any of the fusion proteins of the present invention, and then returning the transfected cells to the individual's body.

In some embodiments, the fusion proteins of the present invention are suitable for treatment of immune system diseases or disorders, including, but not limited to, idiopathic thrombocytopenia purpura, autoimmune neutropenia, autoimmunocytopenia, antiphospholipid syndrome, gluten-sensitive enteropathy, allergic encephalomyelitis, myocarditis, relapsing polychondritis, rheumatic heart disease, neuritis, uveitis ophthalmia, polyendo-crinopathies, purpura (e.g., Henloch-Scoenlein purpura), Reiter's Disease, Stiff-Man Syndrome, autoimmune pulmonary inflammation, myocarditis, IgA glomerulonephritis, dense deposit disease, rheumatic heart disease, Guillain-Barre Syndrome, insulin dependent diabetes mellitus, autoimmune inflammatory eye, autoimmune thyroiditis, hypothyroidism (i.e., Hashimoto's thyroiditis), discoid lupus, Goodpasture's syndrome, pemphigus, receptor autoimmunities (such as, for example, Graves' Disease and insulin resistance), autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI cardiotomy syndrome, urticaria, atopic dermatitis, asthma, inflammatory myopathies, and other inflammatory, granulomatous, degenerative, and atrophic disorders), atherosclerosis and epilepsy.

Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease, Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome).

Examples of inflammatory disorders include chronic inflammatory disorders of the joints, including arthritis, osteoarthritis and bone diseases associated with increased bone resorption; inflammatory bowel diseases such as ileitis, Barrett's syndrome; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma. There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy.

Because a number of immune disorders are caused by inflammation, there is some overlap between disorders that are considered immune diseases and inflammatory diseases. For the purpose of this disclosure, in the case of such an overlapping disorder, the disorder may be considered either an immune disease or an inflammatory disease.

In one embodiment, the fusion proteins of the present invention are used to treat multiple sclerosis.

Mast cells are known to act as antigen-presenting cells and also express PD-L2. In certain pathologic circumstances, it is contemplated that mast cells may also neo-express PD-1. An allergic disorder may include mast cells the express PD-1. Administration of a fusion protein of the invention is contemplated as a therapeutic for such a disorder. Thus, in another embodiment, the fusion proteins of the present invention are used to treat a disorder, the pathology of which pathology includes mast cells that express PD-1. It is also known that T cells play a role in molding mast cell response. Accordingly, it is further contemplated that the fusion protein of the invention may achieve efficacy in diseases including mast cell pathology by an indirect effect, via the effect of the fusion protein on T cell subsets that interface with the pathogenic mast cells in allergic disorders.

In additional embodiments, the fusion proteins of the present invention can be used to treat various types of cancer. Soluble TRAIL has been associated with the induction of apoptosis in certain kinds of tumor cells. Moreover, for certain tumor types, inflammation may actually be pro-tumorigenic. Hence, a TRAIL fusion protein can be used to kill tumor cells directly, block pro-tumorigenic inflammation, and furthermore, can be used to block angiogenesis. The PD-L1 or PD-L2 component (the first domain) in this case would localize the TRAIL to PD-1-positive cells (for example, on antigen-presenting cells or activated T cells themselves).

Soluble FasL has also been associated with the induction of apoptosis in certain kinds of tumor cells. Moreover, for certain tumor types, inflammation may actually be pro-tumorigenic. Hence, a FasL fusion protein can be used to kill tumor cells directly, block pro-tumorigenic inflammation, and furthermore, can be used to block angiogenesis. The PD-L1 or PD-L2 component (the first domain) in this case would localize the FasL to PD-1-positive cells (for example, on antigen-presenting cells or activated T cells themselves).

The terms "cancer" and "cancerous" refer to or describe the physiological condition in mammals that is typically characterized by unregulated cell growth.

The fusion proteins according to the invention may be administered to individuals (such as mammals, including animals and humans) afflicted with a cellular proliferative disorder such as cancer, and malignant and benign tumors. In a particular embodiment of the invention, the individual treated is a human.

Exemplary cancers that may be treated by the fusion proteins, compositions and methods of the invention may also include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia, angioimmunoblastic T-cell lymphoma (AITL), chronic lymphocytic leukemia (CLL), acute nonlymphocytic leukemia, chronic lymphocytic leukemia, acute granulocytic leukemia, chronic granulocytic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, acute promyelocytic leukemia, adult T-cell leukemia, aleukemic leukemia, aleukocythemic leukemia, basophilic leukemia, blast cell leukemia, bovine leukemia, chronic myelocytic leukemia, leukemia cutis, embryonal leukemia, undifferentiated cell leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia and micromyeloblastic leukemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

Various cell types have been found to express PD-1 and may be targeted by the fusion proteins of the invention. These include reactive T cells from Non-Hodgkins lymphoma, neoplastic B cells from small lymphocytic lymphoma, grade III follicular lymphoma and diffuse large cell lymphoma and immune cells from chronic lymphocytic leukemia (B-CLL) (Xerri L., Chetaille B, Serriari N, Attias C, Guillaume Y, Arnoulet C and Olive D, *Human Pathol*, 2008, 39(7): 1050-1058).

For treating cancer, a fusion protein of the invention may be administered to achieve reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Treatment may result in a complete response, defined as disappearance of all signs of cancer, or a partial response, wherein the size of the tumor is decreased, preferably by more than 50 percent, more preferably by 75%. Treatment may also result in the patient experiencing disease stabilization. Parameters for assessing successful treatment and improvement in the disease are readily measurable by routine procedures familiar to a physician of appropriate skill in the art.

The fusion proteins of the present invention are administered in amounts effective to provide improvement in any of the above parameters used to measure success in treatment of cancer, and can be readily determined by one skilled in the art. For example, an effective amount is that amount which is effective in inducing apoptosis in some cancer cells, or a majority of cancer cells, or substantially all of the patient's cancer cells. Other examples of an effective amount include amounts which are effective in reducing proliferation of tumor cells, of halting tumor progression via invasion of other tissues, reducing angiogenesis, and reducing inflammation.

In the context of treatment for cancer, the fusion proteins of the present invention can optionally be administered to a patient in combination with other chemotherapeutic agents. Suitable chemotherapeutic agents include, for example, alkylating agents such as thiotepa and cyclosphosphamide (CYTOXAN™); alkyl sulfonates such as busulfan, improsilfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL.R™, Bristol-Myers Squibb Oncology, Princeton, N.J.) and docetaxel (TAXOTERE.R™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); Ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Chemotherapeutic agents also include chemotherapeutic agents that are able to sensitize tumour cells to TRAIL and overcome TRAIL resistance, such as proteasome inhibitors and histone deacetylase (HDAC) inhibitors, cycloheximide, imatinib mesylate and other protein tyrosine kinase inhibitors, 17-allylamino-17-demethoxygeldanamycin, arsenic trioxide and X-linked Inhibitors of Apoptosis Protein small molecule antagonists; and pharmaceutically acceptable salts, acids or derivatives of any of these.

Additional information on the methods of cancer treatment is provided in U.S. Pat. No. 7,285,522, incorporated by reference in its entirety.

Accordingly, in a preferred embodiment, the fusion proteins of the present invention can be used to treat breast cancer. In another preferred embodiment, the fusion proteins of the invention can be used to treat colon cancer. In another embodiment, the fusion proteins of the invention can be used to treat liver cancer. In another preferred embodiment, the fusion proteins of the invention can be used to treat ovarian cancer. In another embodiment, the fusion proteins of the invention can be used to treat leukemia. In another embodiment, the fusion proteins of the invention can be used to treat melanoma.

In further embodiments, the fusion proteins of the present invention can be used to treat alloimmune diseases, for example graft rejection, or graft-versus-host or host-versus-graft disease.

The practice of the invention is illustrated by the following non-limiting example. The invention should not be construed to be limited solely to the compositions and methods described herein, but should be construed to include other compositions and methods as well. One of skill in the art will know that other compositions and methods are available to perform the procedures described herein.

The example below is described with respect to a representative PD-L1-TRAIL fusion protein. However, a person of skill in the art would understand how to conduct the corresponding experiments with PD-L2-TRAIL, PD-L1-FasL or PD-L2-FasL, or with any other fusion protein of the invention.

EXAMPLES

Materials and Methods

Mice 4-6 week old C57BL/6 female mice were purchased from the Jackson Laboratory (Bar Harbor, Me.), and were maintained under pathogen-free conditions.

Reagents

Plasmids pT2/BH and pNEB 193 UbC-SB 11 are provided by Dr. Perry Hacket (University of Minnesota, Minneapolis), and murine TRAIL cDNAs are obtained from Dr. Hideo Yagita (Juntendo University School of Medicine, Tokyo, Japan). The plasmid pMFneo is obtained from Dr. Herman Waldmann (University of Oxford, Oxford, UK). Mouse MOG 38-50 peptide (GWYRSPFSRVVHL (SEQ ID NO:28)) is synthesized using F-moc solid phase methods and purified by HPLC at Invitrogen Life Technologies (Carlsbad, Calif.). Pertussis toxin may be purchased from EMD Biosciences (San Diego, Calif.). The following reagents are purchased from BD Pharmingen (San Diego, Calif.): ELISA Ab pairs for mouse IL-2, IL-4, IL-6, IFN-.gamma. and recombinant mouse IL-2, IL-4, IL-6, IFN-.gamma. An IL-17 ELISA Ab pairs is obtained from Southern Biotech (Alabama, USA), and recombinant mouse IL-17 is purchased from Biosource (Camarillo, Calif.). PE-anti-mouse TRAIL and PE-anti-mouse PD-L1 are purchased from eBioscience (San Diego, Calif.). Recombinant TRAIL (Super Killer TRAIL™) is purchased from Axxora Platform (San Diego, Calif.).

Plasmid Construction

Chimeric PD-L1-TRAIL and PD-L1-IgG1(mut) coding cassettes are constructed by PCR, using partially overlapping synthetic oligonucleotides. cDNA encoding amino acids (aa) 19-239 of murine PD-L1 (Swiss-prot accession number Q9EP73.1) is joined to cDNA encoding either aa 118-291 of murine TRAIL (Swiss-prot accession number P50592) or a mutated human IgG1 Fc (Fcγ1) segment, respectively. For the latter, a cDNA encoding human Fcγ1 (Brunschwig E B, Levine E, Trefzer U, Tykocinski M L: Glycosylphosphatidylinositol-modified murine B7-1 and B7-2 retain costimulator function, *J. Immunol* 1995, 155: 5498-5505) is modified by PCR-based site-directed mutagenesis, using oligonucleotides configured to mutate C220→S, C226→S, C229→S, N297→A, E233→P, L234→V, and L235→A. To express soluble TRAIL, cDNA encoding aa 118-291 of murine TRAIL is used. All of these cDNA segments are subcloned into a pMFneo eukaryotic expression vector downstream of an EF1α promoter region. Coding sequence for luciferase is mobilized with Hind3- and BamH1 from pTAL-Luc (BD Biosciences; San Jose, Calif.), and subcloned into the respective sites of pMFneo.

To generate a derivative Sleeping Beauty expression vector incorporating within the same plasmid both transposon and transposase cassettes, a transposase coding sequence flanked upstream by a ubiquitin C promoter is generated by PCR from pNEB 193 UbC-SB11 (b.p. 432-2958) and then ligated between the Apal and Xhol sites of pT2/BH vector, which contains a transposon cassette. This new expression vector, incorporating both transposase and transposon expression cassettes, is designated pSBC21. Next, cDNAs corresponding to PD-L1-TRAIL, soluble PD-L1, PD-L1-IgG1(mut), soluble TRAIL, or luciferase, each linked to the EF1α promoter, are subcloned from their respective pMFneo expression constructs into the transposon cassette of pSBC21, downstream of the transposase expression module. All subcloned cDNAs are oriented in the same direction as the transposase.

Cell Culture and Transfection

Human 293 kidney cells and CHO cells are cultured in DMEM and HAM'S F-12, respectively, supplemented with 100 μg/ml penicillin, 100 U/ml streptomycin, 2 and 10% heat-inactivated fetal bovine serum. 293 cells are transiently transfected with the PD-L1-TRAIL, soluble PD-L1, PD-L1-IgG1(mut) and soluble TRAIL pMFneo expression plasmids, using LipofectAMINE™ reagent (Invitrogen Life Technologies, Carlsbad, Calif.). Proteins in conditioned media are resolved by SDS-PAGE and detected by Western blot analysis. Anti-mouse Ab used for detecting PD-L1 and TRAIL are purchased from R&D Systems (Minneapolis, Minn.), respectively.

Induction and Disease Evaluation of EAE EAE is induced according to a standard induction protocol. Stromnes I M, Goverman J M: Active induction of experimental allergic encephalomyelitis, *Nat Protoc* 2006, 1:1810-1819. Briefly, female C57BL/6 mice are challenged with a total of 300 μg of MOG38-50 peptide (divided into two subcutaneous injections, one on each dorsal flank) in 0.1 ml PBS, emulsified in an equal volume of CFA containing 4 mg/ml *Mycobacterium tuberculosis* H37RA (Difco, Detroit, Mich.). These mice are simultaneously injected intravenously with 100 ng of pertussis toxin in 0.2 ml PBS. A second intravenous injection of pertussis toxin (100 ng/mouse) was given 48 h later. Mice are examined daily for signs of EAE and scored.

Cytokine and Proliferation Assay

For cytokine assays, splenocytes are cultured at $1.5 \times 10^6$ cells per well in 0.2 ml of DMEM with 10% FBS, in the presence or absence of different concentrations of MOG38-50 peptide, or 1 μg/ml Con A (Sigma-Aldrich, St. Louis, Mo.). Conditioned media are collected 40 h later, and cytokine concentrations are determined by quantitative ELISA, using paired mAb specific for the corresponding cytokines, per the manufacturer's recommendations (BD Pharmingen, (San Diego, Calif.). Proliferation assays are performed using $0.5 \times 10^6$ cells per well in 96-well plates. [$^3$H] thymidine is added to the cultures at 48 h, and cells are harvested 16 h later. Radioactivity is determined using a flatbed β-counter (Wallac).

Hydrodynamic Injection

Mice are injected with pSBC21 vector alone or pSBC21-based expression constructs incorporating PD-L1-TRAIL, soluble PD-L1, PD-L1-IgG1(mut), soluble TRAIL, or luciferase coding sequences. Expression plasmids are dissolved in saline in a volume (in ml) equivalent to 10% of body weight (in gm). The entire volume for each animal is injected within 5 sec via tail veins, according to a published protocol. Liu F, Song Y, Liu D; Hydrodynamics-based transfection in animals by systemic administration of plasmid DNA, Gene Ther 1999, 6:1258-1266. Retro-orbital blood samples are collected using heparinized glass capillaries. After centrifugation, plasma is recovered and kept at −20° C. until ELISA assays are performed.

Measurement of Recombinant Proteins in Serum

ELISA assays are performed in 96-well microtitration plates For PD-L1-TRAIL, soluble PD-L1, and PD-L1-IgG1 (mut), purified anti-human/mouse PD-L1 receptor Ab from eBioscience (San Diego, Calif.) is used as capture Ab; for soluble TRAIL, anti-mouse TRAIL Ab from R&D Systems (Minneapolis, Minn.) is used as capture Ab. Detecting Ab are: biotin-anti-mouse PD-L1 Ab from eBioscience for PD-L1; biotin-anti-mouse TRAIL Ab from eBioscience for PD-L1-TRAIL and soluble TRAIL; anti-human IgG, Fcγ fragment-specific Ab from Jackson ImmunoResearch Laboratories (West Grove, Pa.) for PD-L1-IgG1(mut).

Capture Ab diluted in coating buffer (0.1 M carbonate, pH 8.2) is distributed in microtitration plates and incubated at 4° C. overnight. After washing twice with 0.05% Tween-20 in PBS, wells are incubated for an additional 2 h at RT with PBS-3% albumin to block nonspecific binding sites. After washing twice again, 100 μl of serum samples are added and incubated at 4° C. overnight. After incubation, wells are rinsed four times and incubated for 1 h with biotinylated detection Ab. For the enzymatic reaction, avidin peroxidase and TMB Microwell peroxidase substrate (KPL, Gaithersburg, Md.) are applied sequentially.

In Vivo Bioluminescence Imaging

Images are acquired at 5 h, 24 h, 5 days, 22 days, 34 days, 51 days, and 1 year after injection of the luciferase expression plasmid. At the time of imaging, mice are anesthetized with ketamine/xylazine. D-luciferin (Biotium, Hayward, Calif.) is dissolved in saline and delivered via intraperitoneal injection before imaging. Mice are then placed in an imaging chamber in which the temperature was maintained at 33° C. Bioluminescent images are acquired using the Xenogen in vivo Imaging System (IVIS; Xenogen Corp, Alameda, Calif.). Imaging parameters are field of view of 8 or 10 cm, exposure time of 4 minutes, number of binning 16, and f1/stop of 1. For display, the luminescent image (pseudo-color) is overlaid on a photographic image, which delineates the anatomic landmarks.

Measurement of Blood-Brain Barrier (BBB) Permeability

BBB permeability is assessed essentially as described (Prasad R, Giri S, Nath N, Singh I, Singh A K: 5-aminoimidazole-4-carboxamide-1-beta-4-ribofuranoside attenuates experimental autoimmune encephalomyelitis via modulation of endothelial-monocyte interaction, *J. Neurosci Res* 2006, 84:614-625), with some modifications. Briefly, on days 6 and 13 after MOG challenge, 4% Evans blue dye (Sigma-Aldrich, St. Louis, Mo.) is injected into the tail veins of C57BL/6 mice. After 1 h, animals are anesthetized and transcardially perfused with saline to remove intravascular dye. Following euthanasia, spinal cords, cerebellums/brainstems and brains are collected. For quantitative measurements, spinal cords are homogenized in 1 ml PBS. Samples are centrifuged once at 15,800 g for 30 min. 600 µl aliquots of the supernatant are then collected and added to 600 ul of 100% TCA (Sigma Aldrich St. Louis, Mo.). This solution is incubated overnight, and centrifuged at 15,800 g for 30 min. Evans blue extravasation is quantified spectrophotometrically (excitation 630 nm and emission 680 nm) in the supernatants.

Preparation and Analysis of Infiltrating Cells from Spinal Cords

Single cell suspensions of spinal cords are prepared as described previously. (Hilliard B, Samoilova E B, Liu T S, Rostami A, Chen Y: Experimental autoimmune encephalomyelitis in NF-kappa B-deficient mice: roles of NF-kappa B in the activation and differentiation of autoreactive T cells, *J Immunol* 1999, 163:2937-2943.) Briefly, mice are sacrificed and spinal cords are removed, placed in ice-cold RPMI medium containing 27% Percoll, and pressed through a 70-µm Falcon cell strainer. The resulting cell suspension is brought to a volume of 50 ml with additional 27% Percoll, mixed, and centrifuged at 300×g for 15 min. The pellet is kept on ice, while the myelin layer and supernatant are transferred to a new 50-ml tube, homogenized by shaking, and centrifuged again at 300×g for 15 min. The cell pellets are then combined and washed three times in RPMI medium at 4° C. For flow cytometric analysis, single cell suspensions of recovered cells are incubated for 45 min with the following Ab: FITC-anti-mouse-IFNγ, PE-anti-mouse IL-10, APC-anti-mouse IL-17, APC-Alexa flour 750-anti-mouse CD4, Percp-cy5.5-anti-mouse CD8, and PE-cy7-anti-mouse CD69, all purchased from eBioscience.

Molecular Modeling of the Chimeric PD-L1-TRAIL Protein

A three-dimensional model of the PD-L1-TRAIL protein is generated using the crystal structure of TRAIL (pdb code: 1DOG) (Hymowitz S G, Christinger H W, Fuh G, Ultsch M, O'Connell M, Kelley R F, Ashkenazi A, de Vos A M: Triggering cell death: the crystal structure of Apo2L/TRAIL in a complex with death receptor 5, Mol Cell 1999, 4:563-571) and a modeled PD-L1 molecule. A three-dimensional model of the ligand binding domain (LBD) of PD-L1 is generated using MODELLER. (Marti-Renom M A, Stuart A C, Fiser A, Sanchez R, Melo F, Sali A: Comparative protein structure modeling of genes and genomes, *Arum Rev Biophys Biomol Struct* 2000, 29:291-325.)

Flow Cytometry and MTT Assays

Immunostaining is performed at 4° C. with specified Ab suspended in PBS containing 0.5% BSA and 0.05% sodium azide (NaN3). All flow cytometric analyses are performed on a FACS Calibur apparatus with Cell Quest software and dual laser (488 and 633 nm) excitation (BD Biosciences). The MTT assay is performed according to the manufacturer's protocol (ATCC, Manassas, Va.).

Statistical Analysis

The Student's t test or Mann-Whitney U test is used to determine the statistical significance of differences A p value of <0.05 was considered to be statistically significant.

Production of Functional PD-L1-TRAIL Protein

Recombinant PD-L1-TRAIL, along with related control proteins (soluble PD-L1, PD-L1-IgG1(mut), soluble TRAIL), are produced using a pMFneo eukaryotic expression system. The chimeric PD-L1-TRAIL coding sequence linked the full extracellular domains of the PD-L1 type I and TRAIL type II membrane proteins, thereby creating a hybrid soluble type I•type II fusion protein. To generate the PD-L1-IgG1(mut) coding sequence, several amino acids within the human IgG1 component are mutated (see Material and Methods) in order to block FcγR binding (and consequent non-specific depletion of lymphocytes) and to interfere with N-glycosylation (which is important for in vivo effector function of human IgG1). Isaacs J D, Greenwood J, Waldmann H: Therapy with monoclonal antibodies. II. The contribution of Fc gamma receptor binding and the influence of C(H)1 and C(H)3 domains on in vivo effector function, *J Immunol* 1998, 161:3862-3869. The various pMFneo-based expression constructs are transiently transfected into 293 cells, and expression and secretion of the respective proteins is demonstrated by Western blot analysis of conditioned media.

To validate the identity of expressed PD-L1-TRAIL, its ability to bind to PD-L1's ligand, PD-1, is assessed. To this end, CHO cells are transiently transfected with a murine PD-1 cDNA expression construct (in the pcDNA3 vector), and after 48 h, transfectants are incubated at 4° C. with purified PD-L1-TRAIL or soluble TRAIL. Immunofluorescence and flow cytometric analysis of these cells, using anti-mouse PD-1 (for PD-1 expression validation) and anti-mouse TRAIL as detecting Ab, may be used to show binding of PD-L1-TRAIL, but not soluble TRAIL, to cell surface PD-1 on transfectants.

The functionality of the TRAIL component of PD-L1-TRAIL is determined by evaluating its capacity to induce apoptosis in mouse EL4 T cells, which constitutively express PD-1 and TRAIL receptor, measuring Annexin V staining by flow cytometry. Recombinant TRAIL (Super Killer TRAIL™) is used as a positive control in this experiment.

Development of a Transposon-Based Expression System for Sustained In Vivo Expression of PD-L1-TRAIL To enable sustained in vivo expression of PD-L1-TRAIL (and control proteins), the transposon-based 'Sleeping Beauty (SB)' expression system is invoked. This system combines the advantages of plasmid-mediated gene delivery together with an ability to integrate into the chromosome and provide for sustained transgene expression. To optimize the efficiency of this expression system, a derivative expression vector is generated, designated pSBC21, that combines within a single plasmid both transposon (accommodating the transgene of interest) and transposase expression cassettes. Since the relative expression level from the two cassettes is important, a number of promoter combinations are screened, and determined that a combination of UBC promoter (driving the transposase) and EF1α promoter (driving the transposon cassette), arrayed in tandem, affords strong transgene expression.

The functionality of this unique dual-cassette transposon/transposase vector derivative (with a UBC/EF1α promoter combination) is validated using a luciferase reporter. A pLuciferase•SBC21 plasmid, at varying concentrations, is administered by hydrodynamic injection to C57BL/6 mice. Hydrodynamic injection of transposon-based expression constructs provides for sustained gene expression in mouse hepatocytes in vivo. Liu F, Song Y, Liu D: Hydrodynamics-based transfection in animals by systemic administration of plasmid DNA, *Gene Ther* 1999, 6:1258-1266. Bioluminescent images acquired after administration of luciferase's substrate, D-Luciferin, reveal luciferase expression.

This vector is used for expressing PD-L1-TRAIL, specifically asking whether levels of PD-L1-TRAIL in serum correlate with the dose of injected pPD-L1-TRAIL•SBC21 plasmid. C57BL/6 mice (in experimental groups of four) are each treated with a single hydrodynamic injection of pPD-L1-TRAIL•SBC21 plasmid, in escalating doses (5, 10 or 20 µg of plasmid). Serum levels of PD-L1-TRAIL are measured by ELISA twenty days after plasmid administration, and a dose-dependent increase in serum PD-L1-TRAIL levels is observed, starting with the 10 µg plasmid dose.

PD-L1-TRAIL Suppresses MOG-Induced Autoimmune Encephalomyelitis

The therapeutic potential of PD-L1-TRAIL in a murine EAE disease model is investigated. To this end, a single encephalitogenic dose of MOG38-50 peptide is administered to C57BL/6 mice. Two days after peptide injection, a single dose of pPD-L1-TRAIL•SBC21 plasmid (50 µg/mouse), or one of four control plasmids (pPD-L1•SBC21, pPD-L1-IgG1(mut)•SBC21, pTRAIL•SBC21, and pSBC21) is administered by hydrodynamic injection. By ELISA, comparable serum levels of expressed proteins in animals hydrodynamically-injected with each of the respective plasmids are detected. Disease progression in the treated mice is monitored by both physical examination and histological analysis of recovered spinal cords.

PD-L1-TRAIL's therapeutic benefit may also be measured from an analysis of day of disease onset and disease incidence.

Assessment of PD-L1-TRAIL is Effectiveness Vs. Its Component Parts, in Combination The question of whether the PD-L1-TRAIL fusion protein's therapeutic efficacy can be recapitulated by administering soluble PD-L1 and TRAIL proteins simultaneously is evaluated, using the same EAE model. Two days after administering a single encephalitogenic challenge of MOG38-50 peptide to C57BL/6 mice, single doses of either pPD-L1-TRAIL•SBC21 plasmid (25 µg/mouse) or a mixture of pPD-L1•SBC21 and pTRAIL•SBC21 plasmids (25 µg each/mouse) are hydrodynamically injected into the animals. This way, it may be demonstrated that PD-L1-TRAIL has substantial therapeutic benefit in preventing EAE induction.

Assessment of PD-L1-TRAIL Effect on Proliferation and Differentiation of Autoreactive T Cells PD-L1-TRAIL's effect on the proliferation and differentiation of myelin-specific T cells recovered from treated animals is assessed. To this end, splenocytes are recovered 43 days after MOG challenge from both PD-L1-TRAIL-treated and control mice receiving vector only. These splenocytes are evaluated in vitro for their proliferation and cytokine production in response to MOG38-50 peptide.

Assessment of PD-L1-TRAIL Effect on Infiltration of Inflammatory Cells into CNS

A key pathologic feature of EAE is infiltration of inflammatory cells into the CNS. PD-L1-TRAIL's effect on this infiltrative process may be assessed. To this end, a comparison may be made of the absolute number of inflammatory cells, along with the percentage of early activated CD4+ and CD8+ cells and of IFNγ-, IL-17- and IL-10-expressing cells, in the spinal cords of PD-L1-TRAIL-versus vector-treated EAE mice on days 7 and 14 post-MOG challenge.

Production and Purification of the Human PD-L1-TRAIL Protein

An expression cassette that may be used to produce human PD-L1-TRAIL is comprised of the coding sequence for the human urokinase signal peptide followed by the coding sequence for human PD-L1-TRAIL. The coding sequences are codon-optimized for enhanced expression in Chinese Hamster Ovary (CHO) cell-lines. The DNA coding sequence is synthesized and then sub-cloned into a mammalian expression vector designed for chromosomal integration and optimized for high level expression in CHO cells.

The PD-L1-TRAIL expression vector is transfected into CHO-S cells, and a clone pool is isolated for initial expression analysis. Out of this clone pool, a high-producing clone is isolated, and expression of the PD-L1-TRAIL protein is analyzed by various methods such as ELISA, SDS-PAGE and Western Blots. Production levels are optimized to reach expression of approximately 100 mg of PD-L1-TRAIL per liter of fermentation media.

Western blot analysis is performed for shake flask culture medium samples obtained from the PD-L1-TRAIL clone grown in various media. The Western blot is probed using a commercial anti-human TRAIL/TNFSF10 Ab as primary detecting antibody.

A high-yield, multi-step chromatographic purification may be used for the isolation of highly-purified PD-L1-TRAIL protein. The process includes an efficient capture step, an anion-exchange chromatography step, and then a final buffer exchange step, the latter carrying the product into the formulation buffer.

A seven-liter production fermentation followed by the above purification process, yields approximately 300 mg of purified PD-L1-TRAIL which may be used for a series of in-vitro and in-vivo experiments indicated below.

EAE Experiments, with Human PD-L1-Trail-Experimental Procedures

EAE is induced in 8-week-old female C57BL/6 mice by injecting subcutaneously, into the left para-lumbar region, 125 ug of myelin oligodendrocyte glycoprotein 35-55 (MOG 35-55) peptide (synthesized by Sigma Laboratories, Israel), emulsified in complete Freund's adjuvant (CFA) containing 5 mg/ml heat-killed *Mycobacterium tuberculosis*. Immediately thereafter, and, again, at 48 hours, the mice are inoculated with 300 ng of pertussis toxin. An additional injection of MOG 35-55 peptide in CFA is delivered 7 days later into the right para-lumbar region. From day 0 to day 8 mice are injected subcutaneously with 50, 100 or 200 micrograms a day of human PD-L1-TRAIL (human PD-L1 and human TRAIL bind mouse PD-1 and mouse TRAIL receptor, respectively) or vehicle, in two equal doses (n=4 in each group). On day 9 the mice are treated for the last time, and sacrificed an hour later. Spleens are harvested and weighed. Pooled lymph node cells (LNCs) are prepared from inguinal, axillary and mesenteric lymph nodes or from spleens of mice that have been inoculated 9 days earlier with MOG35-55 peptide in CFA with or without PD-L1-TRAIL treatment. The ex vivo response of the lymphocytes is assayed in triplicate wells of 96-well flat-bottom plates. A total of $2\times10^5$ cells, suspended in 0.2 ml RPMI supplemented with 1% penicillin streptomycin, 1% glutamine and 5% fetal calf serum (FCS) and beta-mercapto-ethanol are added to each well. After 48 hrs, 1 µCi 3(H)Thymidine (Amersham, UK) is added to each well and the plates are incubated for an additional 18 hrs. Plates are then harvested with a semi-automatic harvester onto a glass fiber filter and the radioactivity is determined by liquid scintillation. The results are expressed as Stimulation Index (SI) according to the equation: SI=Mean cpm of the stimulated cells/mean cpm of the unstimulated cells.

Pooled spleen lymphocytes are isolated, using a Ficoll-Hipaque gradient, on day 9 from MOG-immunized mice treated with PD-L1-Trail (n=4 animals in each group). Recovered cells are stained with methylene blue and counted.

Pooled lymphocytes isolated from lymph nodes recovered on day 9 of PD-L1-Trail treatment in MOG-immunized mice (n=4 in each group) are stimulated for 72 hrs with MOG peptide. Cultures are pulsed with [$^3$H]-thymidine 18 hrs before the end of incubation. Proliferation is estimated by [$^3$H]thymidine incorporation and is expressed as stimulation index (mean cpm of stimulated cells/mean cpm of non-stimulated cells; SI>2 represents significant stimulation).

EAE is induced by MOG challenge, as described above. On day 10 after MOG administration, mice (10 in each group) are treated with either vehicle or PD-L1-Trail at 25, 50 and 100 µg/day, in two divided doses. Mice are followed daily for the evaluation of their clinical disease scores. The clinical status of mice is graded as follows: 0, no signs of disease; 1, tail weakness; 2, hind limb weakness sufficient to impair righting; 3, hind limb paresis; 4, paraplegia with forelimb weakness; 5, quadriplegia; 6, death. Treatment is stopped on day 26 after disease induction (day 16 of PD-L1-Trail treatment).

Collagen-Induced Arthritis with PD-L1-Trail—Experimental Procedures

DBA1 male mice are challenged twice (3 weeks apart) with 200 ug of type II collagen purified from bovine articular cartilage and emulsified in complete Freund's adjuvant (CFA: Difco Labs), via intradermal injection at the base of the tail. Mice are followed daily and monitored for swelling and/or erythema in one or more limbs. On the day of disease onset, mice are randomized for control group (treated with vehicle only) and treatment groups (one daily dose of 100 or 200 ug/mice/d of PD-L1-Trail). Both vehicle and PD-L1-Trail are administered subcutaneously. Injections are given daily for 14 days to the control and 100 ug group, and for 7 days to the 200 ug group. Mice are followed daily for 14 days from disease onset, and then every 3 days. Swelling in all 4 limbs is measured using a microcaliper, and compared to healthy, age-matched mice. The delta of swelling in each limb is calculated, and these deltas are summed into a score (disease index).

Assay for PD-L1-TRAIL-Driven Cytotoxicity Against Cancer Cells

Tumor cell cytotoxicity mediated by purified untagged human PD-L1-TRAIL protein is studied with several human tumor cell types. Human leukemia cell lines are incubated with increasing concentrations of purified PD-L1-TRAIL, and the EC50 is measured.

Assessment of PD-L1-TRAIL's Tumoricidal Activity Vs. Its Component Parts in Combination The tumoricidal effect of the PD-L1-TRAIL fusion protein is compared to the effect of its component parts added in combination. To this end, cell viability of the hepatoma cancer cell line SK-Hep1 is measured following incubation with either purified PD-L1-TRAIL, soluble extracellular domain of TRAIL (sTRAIL) alone, soluble PD-L1 fused to the Fc domain of IgG1 (PD-L1-Fc), or the combination of both (PD-L1-Fc+sTRAIL), at similar molar concentrations.

Apoptosis Assay

Cells of the human hepatoma cancer cell line SK-Hep1 are incubated with increasing concentrations of purified PD-L1-TRAIL, soluble PD-L1 fused to the Fc domain of IgG (PD-L1-Fc) alone, the soluble extracellular domain of TRAIL (sTRAIL) alone, or a combination of both (PD-L1-Fc+sTRAIL). Following incubation with the respective proteins, the treated cells are analyzed by FACS to determine the percentage of cells undergoing apoptosis, as assessed by annexin V/PI staining.

The disclosures of each and every patent, patent application, publication, GenBank UniProtKB, or SwissProt record cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed is:

1. A fusion protein comprising a first domain and a second domain, wherein the first domain comprises a polypeptide that binds to and triggers PD-1 and the second domain comprises a polypeptide that binds to and triggers a TRAIL receptor, wherein the polypeptide that binds to and triggers PD-1 comprises amino acids 1-220 of SEQ ID NO: 5 and the polypeptide that binds to and triggers a TRAIL receptor comprises the amino acid sequence of SEQ ID NO: 15.

2. The fusion protein according to claim 1, wherein the fusion protein comprises the amino acid sequence of SEQ ID NO:5, SEQ ID NO:6, SEQ ID NO:7 or SEQ ID NO:8.

3. The fusion protein according to claim 1, wherein the first domain and the second domain are connected via a linker.

4. The fusion protein according to claim 3, wherein the linker is a protein linker.

5. A pharmaceutical composition comprising a pharmaceutically acceptable carrier and a fusion protein according to claim 1.

6. A pharmaceutical composition comprising a fusion protein according to claim 1, for treating an autoimmune or alloimmune disease.

7. A pharmaceutical composition comprising a fusion protein according to claim 1, for treating an inflammatory disease.

8. A pharmaceutical composition comprising a fusion protein according to claim 1, for treating cancer.

9. A pharmaceutical composition comprising a pharmaceutically acceptable carrier and a fusion protein according to claim 2.

* * * * *

SEQUENCE LISTING

```
<160> NUMBER OF SEQ ID NOS: 28

<210> SEQ ID NO 1
<211> LENGTH: 410
<212> TYPE: PRT
<213> ORGANISM: Artificial Sequence
<220> FEATURE:
<223> OTHER INFORMATION: PD-L1/TRAIL fusion protein

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60
```

```
Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Glu Thr Ile Ser Thr Val Gln Glu Lys Gln Gln Asn Ile Ser
225                 230                 235                 240

Pro Leu Val Arg Glu Arg Gly Pro Gln Arg Val Ala Ala His Ile Thr
                245                 250                 255

Gly Thr Arg Gly Arg Ser Asn Thr Leu Ser Ser Pro Asn Ser Lys Asn
            260                 265                 270

Glu Lys Ala Leu Gly Arg Lys Ile Asn Ser Trp Glu Ser Ser Arg Ser
        275                 280                 285

Gly His Ser Phe Leu Ser Asn Leu His Leu Arg Asn Gly Glu Leu Val
    290                 295                 300

Ile His Glu Lys Gly Phe Tyr Tyr Ile Tyr Ser Gln Thr Tyr Phe Arg
305                 310                 315                 320

Phe Gln Glu Glu Ile Lys Glu Asn Thr Lys Asn Asp Lys Gln Met Val
                325                 330                 335

Gln Tyr Ile Tyr Lys Tyr Thr Ser Tyr Pro Asp Pro Ile Leu Leu Met
            340                 345                 350

Lys Ser Ala Arg Asn Ser Cys Trp Ser Lys Asp Ala Glu Tyr Gly Leu
        355                 360                 365

Tyr Ser Ile Tyr Gln Gly Gly Ile Phe Glu Leu Lys Glu Asn Asp Arg
    370                 375                 380

Ile Phe Val Ser Val Thr Asn Glu His Leu Ile Asp Met Asp His Glu
385                 390                 395                 400

Ala Ser Phe Phe Gly Ala Phe Leu Val Gly
                405                 410

<210> SEQ ID NO 2
<211> LENGTH: 391
<212> TYPE: PRT
<213> ORGANISM: Artificial Sequence
<220> FEATURE:
<223> OTHER INFORMATION: PD-L1/TRAIL fusion protein

<400> SEQUENCE: 2

Met Arg Ile Phe Ala Val Phe Ile Phe Met Thr Tyr Trp His Leu Leu
 1               5                  10                  15
```

```
Asn Ala Phe Thr Val Thr Val Pro Lys Asp Leu Tyr Val Val Glu Tyr
             20                  25                  30
Gly Ser Asn Met Thr Ile Glu Cys Lys Phe Pro Val Glu Lys Gln Leu
         35                  40                  45
Asp Leu Ala Ala Leu Ile Val Tyr Trp Glu Met Glu Asp Lys Asn Ile
 50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
        115                 120                 125
Lys Val Asn Ala Pro Tyr Asn Lys Ile Asn Gln Arg Ile Leu Val Val
130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
210                 215                 220
Val Ile Arg Gly Pro Gln Arg Val Ala Ala His Ile Thr Gly Thr Arg
225                 230                 235                 240
Gly Arg Ser Asn Thr Leu Ser Ser Pro Asn Ser Lys Asn Glu Lys Ala
                245                 250                 255
Leu Gly Arg Lys Ile Asn Ser Trp Glu Ser Ser Arg Ser Gly His Ser
            260                 265                 270
Phe Leu Ser Asn Leu His Leu Arg Asn Gly Glu Leu Val Ile His Glu
        275                 280                 285
Lys Gly Phe Tyr Tyr Ile Tyr Ser Gln Thr Tyr Phe Arg Phe Gln Glu
290                 295                 300
Glu Ile Lys Glu Asn Thr Lys Asn Asp Lys Gln Met Val Gln Tyr Ile
305                 310                 315                 320
Tyr Lys Tyr Thr Ser Tyr Pro Asp Pro Ile Leu Leu Met Lys Ser Ala
                325                 330                 335
Arg Asn Ser Cys Trp Ser Lys Asp Ala Glu Tyr Gly Leu Tyr Ser Ile
            340                 345                 350
Tyr Gln Gly Gly Ile Phe Glu Leu Lys Glu Asn Asp Arg Ile Phe Val
        355                 360                 365
Ser Val Thr Asn Glu His Leu Ile Asp Met Asp His Glu Ala Ser Phe
370                 375                 380
Phe Gly Ala Phe Leu Val Gly
385                 390

<210> SEQ ID NO 3
<211> LENGTH: 447
<212> TYPE: PRT
<213> ORGANISM: Artificial Sequence
<220> FEATURE:
<223> OTHER INFORMATION: PD-L1/TRAIL fusion protein
```

<400> SEQUENCE: 3

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Gly Asp Pro Leu Val Thr Ala Ala Ser Val Leu Glu Phe Gly
225                 230                 235                 240

Gly Ser Gly Gly Gly Ser Glu Gly Gly Gly Ser Glu Gly Gly Gly Ser
                245                 250                 255

Glu Gly Gly Gly Ser Asp Ile Glu Thr Ile Ser Thr Val Gln Glu Lys
            260                 265                 270

Gln Gln Asn Ile Ser Pro Leu Val Arg Glu Arg Gly Pro Gln Arg Val
        275                 280                 285

Ala Ala His Ile Thr Gly Thr Arg Gly Arg Ser Asn Thr Leu Ser Ser
    290                 295                 300

Pro Asn Ser Lys Asn Glu Lys Ala Leu Gly Arg Lys Ile Asn Ser Trp
305                 310                 315                 320

Glu Ser Ser Arg Ser Gly His Ser Phe Leu Ser Asn Leu His Leu Arg
                325                 330                 335

Asn Gly Glu Leu Val Ile His Glu Lys Gly Phe Tyr Tyr Ile Tyr Ser
            340                 345                 350

Gln Thr Tyr Phe Arg Phe Gln Glu Glu Ile Lys Glu Asn Thr Lys Asn
        355                 360                 365

Asp Lys Gln Met Val Gln Tyr Ile Tyr Lys Tyr Thr Ser Tyr Pro Asp
370                 375                 380

Pro Ile Leu Leu Met Lys Ser Ala Arg Asn Ser Cys Trp Ser Lys Asp
385                 390                 395                 400

Ala Glu Tyr Gly Leu Tyr Ser Ile Tyr Gln Gly Gly Ile Phe Glu Leu
```

```
                    405                 410                 415
Lys Glu Asn Asp Arg Ile Phe Val Ser Tyr Thr Asn Glu His Leu Ile
            420                 425                 430

Asp Met Asp His Glu Ala Ser Phe Phe Gly Ala Phe Leu Val Gly
            435                 440                 445

<210> SEQ ID NO 4
<211> LENGTH: 426
<212> TYPE: PRT
<213> ORGANISM: Artificial Sequence
<220> FEATURE:
<223> OTHER INFORMATION: PD-L1/TRAIL fusion protein

<400> SEQUENCE: 4

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Asp Ala Gly Val Tyr Arg
            100                 105                 110

Cys Met Ile Ser Tyr Gly Gly Ala Asp Tyr Lys Arg Ile Thr Val Lys
        115                 120                 125

Val Asn Ala Pro Tyr Asn Lys Ile Asn Gln Arg Ile Leu Val Val Asp
    130                 135                 140

Pro Val Gly Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr Cys
        195                 200                 205

Thr Phe Arg Arg Leu Asp Pro Glu Glu Asn His Thr Ala Glu Leu Val
    210                 215                 220

Ile Gly Asp Pro Leu Val Thr Ala Ala Ser Val Leu Glu Phe Gly Gly
225                 230                 235                 240

Ser Gly Gly Gly Ser Glu Gly Gly Ser Glu Gly Gly Ser Glu
                245                 250                 255

Gly Gly Gly Ser Asp Ile Arg Gly Gln Arg Val Ala Ala His Ile Thr
            260                 265                 270

Gly Thr Arg Gly Arg Ser Asn Thr Leu Ser Ser Pro Asn Ser Lys Asn
        275                 280                 285

Glu Lys Ala Leu Gly Arg Lys Ile Asn Ser Trp Glu Ser Ser Arg Ser
    290                 295                 300

Gly His Ser Phe Leu Ser Asn Leu His Leu Arg Asn Gly Glu Leu Val
305                 310                 315                 320

Ile His Glu Lys Gly Phe Tyr Tyr Ile Tyr Ser Gln Thr Tyr Phe Arg
```

```
                    325                 330                 335
Phe Gln Glu Glu Ile Lys Glu Asn Thr Lys Asn Asp Lys Gln Met Val
                340                 345                 350

Gln Tyr Ile Tyr Lys Tyr Thr Ser Tyr Pro Asp Pro Ile Leu Leu Met
            355                 360                 365

Lys Ser Ala Arg Asn Ser Cys Trp Ser Lys Asp Ala Glu Tyr Gly Leu
        370                 375                 380

Tyr Ser Ile Tyr Gln Gly Gly Ile Phe Glu Leu Lys Glu Asn Asp Arg
385                 390                 395                 400

Ile Phe Val Ser Val Thr Asn Glu His Leu Ile Asp Met Asp His Glu
                405                 410                 415

Ala Ser Phe Phe Gly Ala Phe Leu Val Gly
                420                 425

<210> SEQ ID NO 5
<211> LENGTH: 402
<212> TYPE: PRT
<213> ORGANISM: Artificial Sequence
<220> FEATURE:
<223> OTHER INFORMATION: PD-L2/TRAIL fusion protein

<400> SEQUENCE: 5

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Lys Val Glu Asn Asp
    50                  55                  60

Thr Ser Pro His Arg Glu Arg Ala Thr Leu Leu Glu Glu Gln Leu Pro
65                  70                  75                  80

Leu Gly Lys Ala Ser Phe His Ile Pro Gln Val Gln Val Arg Asp Glu
                85                  90                  95

Gly Gln Tyr Gln Cys Ile Ile Ile Tyr Gly Val Ala Trp Asp Tyr Lys
            100                 105                 110

Tyr Leu Thr Leu Lys Val Lys Ala Ser Tyr Arg Lys Ile Asn Thr His
        115                 120                 125

Ile Leu Lys Val Pro Glu Thr Asp Glu Val Glu Leu Thr Cys Gln Ala
    130                 135                 140

Thr Gly Tyr Pro Leu Ala Glu Val Ser Trp Pro Asn Val Ser Val Pro
145                 150                 155                 160

Ala Asn Thr Ser His Ser Arg Thr Pro Glu Gly Leu Tyr Gln Val Thr
                165                 170                 175

Ser Val Leu Arg Leu Lys Pro Pro Gly Arg Asn Phe Ser Cys Val
            180                 185                 190

Phe Trp Asn Thr His Val Arg Glu Leu Thr Ala Ser Ile Asp Leu Gln
        195                 200                 205

Ser Gln Met Glu Pro Arg Thr His Pro Thr Glu Thr Ile Ser Thr Val
    210                 215                 220

Gln Glu Lys Gln Gln Asn Ile Ser Pro Leu Val Arg Glu Arg Gly Pro
225                 230                 235                 240

Gln Arg Val Ala Ala His Ile Thr Gly Thr Arg Gly Arg Ser Asn Thr
                245                 250                 255

Leu Ser Ser Pro Asn Ser Lys Asn Glu Lys Ala Leu Gly Arg Lys Ile
```

```
                    260                 265                 270
Asn Ser Trp Glu Ser Ser Arg Ser Gly His Ser Phe Leu Ser Asn Leu
            275                 280                 285
His Leu Arg Asn Gly Glu Leu Val Ile His Glu Lys Gly Phe Tyr Tyr
        290                 295                 300
Ile Tyr Ser Gln Thr Tyr Phe Arg Phe Gln Glu Ile Lys Glu Asn
305                 310                 315                 320
Thr Lys Asn Asp Lys Gln Met Val Gln Tyr Ile Tyr Lys Tyr Thr Ser
                325                 330                 335
Tyr Pro Asp Pro Ile Leu Leu Met Lys Ser Ala Arg Asn Ser Cys Trp
            340                 345                 350
Ser Lys Asp Ala Glu Tyr Gly Leu Tyr Ser Ile Tyr Gln Gly Gly Ile
        355                 360                 365
Phe Glu Leu Lys Glu Asn Asp Arg Ile Phe Val Ser Val Thr Asn Glu
    370                 375                 380
His Leu Ile Asp Met Asp His Glu Ala Ser Phe Phe Gly Ala Phe Leu
385                 390                 395                 400
Val Gly

<210> SEQ ID NO 6
<211> LENGTH: 385
<212> TYPE: PRT
<213> ORGANISM: Artificial Sequence
<220> FEATURE:
<223> OTHER INFORMATION: PD-L2/TRAIL fusion protein

<400> SEQUENCE: 6

Met Ile Phe Leu Leu Ile Met Leu Ser Leu Glu Leu Gln Leu His Gln
1               5                   10                  15
Ile Ala Ala Leu Phe Thr Val Thr Val Pro Lys Glu Leu Tyr Ile Ile
            20                  25                  30
Glu His Gly Ser Asn Val Thr Leu Glu Cys Asn Phe Asp Thr Gly Ser
        35                  40                  45
His Val Asn Leu Gly Ala Ile Thr Ala Ser Leu Gln Lys Val Glu Asn
    50                  55                  60
Asp Thr Ser Pro His Arg Glu Arg Ala Thr Leu Leu Glu Glu Gln Leu
65                  70                  75                  80
Pro Leu Gly Lys Ala Ser Phe His Ile Pro Gln Val Gln Val Arg Asp
                85                  90                  95
Glu Gly Gln Tyr Gln Cys Ile Ile Ile Tyr Gly Val Ala Trp Asp Tyr
            100                 105                 110
Lys Tyr Leu Thr Leu Lys Val Lys Ala Ser Tyr Arg Lys Ile Asn Thr
        115                 120                 125
His Ile Leu Lys Val Pro Glu Thr Asp Glu Val Glu Leu Thr Cys Gln
    130                 135                 140
Ala Thr Gly Tyr Pro Leu Ala Glu Val Ser Trp Pro Asn Val Ser Val
145                 150                 155                 160
Pro Ala Asn Thr Ser His Ser Arg Thr Pro Glu Gly Leu Tyr Gln Val
                165                 170                 175
Thr Ser Val Leu Arg Leu Lys Pro Pro Pro Gly Arg Asn Phe Ser Cys
            180                 185                 190
Val Phe Trp Asn Thr His Val Arg Glu Leu Thr Leu Ala Ser Ile Asp
        195                 200                 205
Leu Gln Ser Gln Met Glu Pro Arg Thr His Pro Thr Arg Gly Pro Gln
    210                 215                 220
```

```
Arg Val Ala Ala His Ile Thr Gly Thr Arg Gly Arg Ser Asn Thr Leu
225                 230                 235                 240

Ser Ser Pro Asn Ser Lys Asn Glu Lys Ala Leu Gly Arg Lys Ile Asn
            245                 250                 255

Ser Trp Glu Ser Ser Arg Ser Gly His Ser Phe Leu Ser Asn Leu His
        260                 265                 270

Leu Arg Asn Gly Glu Leu Val Ile His Glu Lys Gly Phe Tyr Tyr Ile
    275                 280                 285

Tyr Ser Gln Thr Tyr Phe Arg Phe Gln Glu Glu Ile Lys Glu Asn Thr
290                 295                 300

Lys Asn Asp Lys Gln Met Val Gln Tyr Ile Tyr Lys Tyr Thr Ser Tyr
305                 310                 315                 320

Pro Asp Pro Ile Leu Leu Met Lys Ser Ala Arg Asn Ser Cys Trp Ser
                325                 330                 335

Lys Asp Ala Glu Tyr Gly Leu Tyr Ser Ile Tyr Gln Gly Gly Ile Phe
            340                 345                 350

Glu Leu Lys Glu Asn Asp Arg Ile Phe Val Ser Val Thr Asn Glu His
        355                 360                 365

Leu Ile Asp Met Asp His Glu Ala Ser Phe Phe Gly Ala Phe Leu Val
    370                 375                 380

Gly
385

<210> SEQ ID NO 7
<211> LENGTH: 441
<212> TYPE: PRT
<213> ORGANISM: Artificial Sequence
<220> FEATURE:
<223> OTHER INFORMATION: PD-L2/TRAIL fusion protein

<400> SEQUENCE: 7

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190
```

```
Val Phe Trp Asn Thr His Val Arg Glu Leu Thr Leu Ala Ser Ile Asp
            195                 200                 205

Leu Gln Ser Gln Met Glu Pro Arg Thr His Pro Thr Gly Asp Pro Leu
210                 215                 220

Val Thr Ala Ala Ser Val Leu Glu Phe Gly Ser Gly Gly Gly Gly Ser
225                 230                 235                 240

Glu Gly Gly Gly Ser Glu Gly Gly Ser Glu Gly Gly Gly Ser Asp
                245                 250                 255

Ile Glu Thr Ile Ser Thr Val Gln Glu Lys Gln Gln Asn Ile Ser Pro
            260                 265                 270

Leu Val Arg Glu Arg Gly Pro Gln Arg Val Ala Ala His Ile Thr Gly
275                 280                 285

Thr Arg Gly Arg Ser Asn Thr Leu Ser Ser Pro Asn Ser Lys Asn Glu
290                 295                 300

Lys Ala Leu Gly Arg Lys Ile Asn Ser Trp Glu Ser Ser Arg Ser Gly
305                 310                 315                 320

His Ser Phe Leu Ser Asn Leu His Leu Arg Asn Gly Glu Leu Val Ile
                325                 330                 335

His Glu Lys Gly Phe Tyr Tyr Ile Tyr Ser Gln Thr Tyr Phe Arg Phe
            340                 345                 350

Gln Glu Glu Ile Lys Glu Asn Thr Lys Asn Asp Lys Gln Met Val Gln
355                 360                 365

Tyr Ile Tyr Lys Tyr Thr Ser Tyr Pro Asp Pro Ile Leu Leu Met Lys
370                 375                 380

Ser Ala Arg Asn Ser Cys Trp Ser Lys Asp Ala Glu Tyr Gly Leu Tyr
385                 390                 395                 400

Ser Ile Tyr Gln Gly Gly Ile Phe Glu Leu Lys Glu Asn Asp Arg Ile
                405                 410                 415

Phe Val Ser Val Thr Asn Glu His Leu Ile Asp Met Asp His Glu Ala
            420                 425                 430

Ser Phe Phe Gly Ala Phe Leu Val Gly
                435                 440

<210> SEQ ID NO 8
<211> LENGTH: 422
<212> TYPE: PRT
<213> ORGANISM: Artificial Sequence
<220> FEATURE:
<223> OTHER INFORMATION: PD-L2/TRAIL fusion protein

<400> SEQUENCE: 8

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
                100                 105                 110
```

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
        130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Gly Asp Pro Leu
    210                 215                 220

Val Thr Ala Ala Ser Val Leu Glu Phe Gly Ser Gly Gly Gly Gly Ser
225                 230                 235                 240

Glu Gly Gly Gly Ser Glu Gly Gly Gly Ser Glu Gly Gly Gly Ser Asp
                245                 250                 255

Ile Arg Gly Pro Gln Arg Val Ala Ala His Ile Thr Gly Thr Arg Gly
            260                 265                 270

Arg Ser Asn Thr Leu Ser Ser Pro Asn Ser Lys Asn Glu Lys Ala Leu
        275                 280                 285

Gly Arg Lys Ile Asn Ser Trp Glu Ser Ser Arg Ser Gly His Ser Phe
    290                 295                 300

Leu Ser Asn Leu His Leu Arg Asn Gly Glu Leu Val Ile His Glu Lys
305                 310                 315                 320

Gly Phe Tyr Tyr Ile Tyr Ser Gln Thr Tyr Phe Arg Phe Gln Glu Glu
                325                 330                 335

Ile Lys Glu Asn Thr Lys Asn Asp Lys Gln Met Val Gln Tyr Ile Tyr
            340                 345                 350

Lys Tyr Thr Ser Tyr Pro Asp Pro Ile Leu Leu Met Lys Ser Ala Arg
        355                 360                 365

Asn Ser Cys Trp Ser Lys Asp Ala Glu Tyr Gly Leu Tyr Ser Ile Tyr
    370                 375                 380

Gln Gly Gly Ile Phe Glu Leu Lys Glu Asn Asp Arg Ile Phe Val Ser
385                 390                 395                 400

Val Thr Asn Glu His Leu Ile Asp Met Asp His Glu Ala Ser Phe Phe
                405                 410                 415

Gly Ala Phe Leu Val Gly
            420

<210> SEQ ID NO 9
<211> LENGTH: 381
<212> TYPE: PRT
<213> ORGANISM: Artificial Sequence
<220> FEATURE:
<223> OTHER INFORMATION: PD-L1/FasL fusion protein

<400> SEQUENCE: 9

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45
```

-continued

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Leu Glu Lys Gln Ile Gly His Pro Ser Pro Pro Pro Glu Lys
225                 230                 235                 240

Lys Glu Leu Arg Lys Val Ala His Leu Thr Gly Lys Ser Asn Ser Arg
                245                 250                 255

Ser Met Pro Leu Glu Trp Glu Asp Thr Tyr Gly Ile Val Leu Leu Ser
            260                 265                 270

Gly Val Lys Tyr Lys Lys Gly Gly Leu Val Ile Asn Glu Thr Gly Leu
        275                 280                 285

Tyr Phe Val Tyr Ser Lys Val Tyr Phe Arg Gly Gln Ser Cys Asn Asn
290                 295                 300

Leu Pro Leu Ser His Lys Val Tyr Met Arg Asn Ser Lys Tyr Pro Gln
305                 310                 315                 320

Asp Leu Val Met Met Glu Gly Lys Met Met Ser Tyr Cys Thr Thr Gly
                325                 330                 335

Gln Met Trp Ala Arg Ser Ser Tyr Leu Gly Ala Val Phe Asn Leu Thr
            340                 345                 350

Ser Ala Asp His Leu Tyr Val Asn Val Ser Glu Leu Ser Leu Val Asn
        355                 360                 365

Phe Glu Glu Ser Gln Thr Phe Phe Gly Leu Tyr Lys Leu
370                 375                 380

<210> SEQ ID NO 10
<211> LENGTH: 418
<212> TYPE: PRT
<213> ORGANISM: Artificial Sequence
<220> FEATURE:
<223> OTHER INFORMATION: PD-L1/FasL fusion protein

<400> SEQUENCE: 10

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

-continued

Gly Ser Asn Met Thr Ile Glu Cys Lys Phe Pro Val Glu Lys Gln Leu
                35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
210                 215                 220

Val Ile Gly Asp Pro Leu Val Thr Ala Ala Ser Val Leu Glu Phe Gly
225                 230                 235                 240

Gly Ser Gly Gly Gly Ser Glu Gly Gly Gly Ser Glu Gly Gly Gly Ser
                245                 250                 255

Glu Gly Gly Gly Ser Asp Ile Leu Glu Lys Gln Ile Gly His Pro Ser
                260                 265                 270

Pro Pro Pro Glu Lys Lys Glu Leu Arg Lys Val Ala His Leu Thr Gly
                275                 280                 285

Lys Ser Asn Ser Arg Ser Met Pro Leu Glu Trp Glu Asp Thr Tyr Gly
                290                 295                 300

Ile Val Leu Leu Ser Gly Val Lys Tyr Lys Lys Gly Gly Leu Val Ile
305                 310                 315                 320

Asn Glu Thr Gly Leu Tyr Phe Val Tyr Ser Lys Val Tyr Phe Arg Gly
                325                 330                 335

Gln Ser Cys Asn Asn Leu Pro Leu Ser His Lys Val Tyr Met Arg Asn
                340                 345                 350

Ser Lys Tyr Pro Gln Asp Leu Val Met Met Glu Gly Lys Met Met Ser
                355                 360                 365

Tyr Cys Thr Thr Gly Gln Met Trp Ala Arg Ser Ser Tyr Leu Gly Ala
                370                 375                 380

Val Phe Asn Leu Thr Ser Ala Asp His Leu Tyr Val Asn Val Ser Glu
385                 390                 395                 400

Leu Ser Leu Val Asn Phe Glu Glu Ser Gln Thr Phe Phe Gly Leu Tyr
                405                 410                 415

Lys Leu

<210> SEQ ID NO 11
<211> LENGTH: 375
<212> TYPE: PRT

<213> ORGANISM: Artificial Sequence
<220> FEATURE:
<223> OTHER INFORMATION: PD-L2/FasL fusion protein

<400> SEQUENCE: 11

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr

<210> SEQ ID NO 12
<211> LENGTH: 412
<212> TYPE: PRT
<213> ORGANISM: Artificial Sequence
<220> FEATURE:
<223> OTHER INFORMATION: PD-L2/FasL fusion protein

<400> SEQUENCE: 12

| Met | Ile | Phe | Leu | Leu | Leu | Met | Leu | Ser | Leu | Glu | Leu | Gln | Leu | His | Gln |
|---|---|---|---|---|---|---|---|---|---|---|---|---|---|---|---|
| 1 | | | | 5 | | | | | 10 | | | | | 15 | |

| Ile | Ala | Ala | Leu | Phe | Thr | Val | Thr | Val | Pro | Lys | Glu | Leu | Tyr | Ile | Ile |
| | | | 20 | | | | | 25 | | | | | 30 | | |

| Glu | His | Gly | Ser | Asn | Val | Thr | Leu | Gl

```
                    370                 375                 380
Ala Asp His Leu Tyr Val Asn Val Ser Glu Leu Ser Leu Val Asn Phe
385                 390                 395                 400

Glu Glu Ser Gln Thr Phe Phe Gly Leu Tyr Lys Leu
                    405                 410

<210> SEQ ID NO 13
<211> LENGTH: 281
<212> TYPE: PRT
<213> ORGANISM: Homo sapiens

<400> SEQUENCE: 13

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Gly Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 14
<211> LENGTH: 184
<212> TYPE: PRT
<213> ORGANISM: Artificial Sequence
<220> FEATURE:
<223> OTHER INFORMATION: fragment of SEQ ID NO: 13

<400> SEQUENCE: 14
```

```
Glu Thr Ile Ser Thr Val Gln Glu Lys Gln Gln Asn Ile Ser Pro Leu
1               5                   10                  15

Val Arg Glu Arg Gly Pro Gln Arg Val Ala Ala His Ile Thr Gly Thr
            20                  25                  30

Arg Gly Arg Ser Asn Thr Leu Ser Ser Pro Asn Ser Lys Asn Glu Lys
        35                  40                  45

Ala Leu Gly Arg Lys Ile Asn Ser Trp Glu Ser Ser Arg Ser Gly His
50                  55                  60

Ser Phe Leu Ser Asn Leu His Leu Arg Asn Gly Glu Leu Val Ile His
65                  70                  75                  80

Glu Lys Gly Phe Tyr Tyr Ile Tyr Ser Gln Thr Tyr Phe Arg Phe Gln
                85                  90                  95

Glu Glu Ile Lys Glu Asn Thr Lys Asn Asp Lys Gln Met Val Gln Tyr
            100                 105                 110

Ile Tyr Lys Tyr Thr Ser Tyr Pro Asp Pro Ile Leu Leu Met Lys Ser
        115                 120                 125

Ala Arg Asn Ser Cys Trp Ser Lys Asp Ala Glu Tyr Gly Leu Tyr Ser
130                 135                 140

Ile Tyr Gln Gly Gly Ile Phe Glu Leu Lys Glu Asn Asp Arg Ile Phe
145                 150                 155                 160

Val Ser Val Thr Asn Glu His Leu Ile Asp Met Asp His Glu Ala Ser
                165                 170                 175

Phe Phe Gly Ala Phe Leu Val Gly
                180

<210> SEQ ID NO 15
<211> LENGTH: 165
<212> TYPE: PRT
<213> ORGANISM: Artificial Sequence
<220> FEATURE:
<223> OTHER INFORMATION: fragment of SEQ ID NO: 13

<400> SEQUENCE: 15

Arg Gly Pro Gln Arg Val Ala Ala His Ile Thr Gly Thr Arg Gly Arg
1               5                   10                  15

Ser Asn Thr Leu Ser Ser Pro Asn Ser Lys Asn Glu Lys Ala Leu Gly
            20                  25                  30

Arg Lys Ile Asn Ser Trp Glu Ser Ser Arg Ser Gly His Ser Phe Leu
        35                  40                  45

Ser Asn Leu His Leu Arg Asn Gly Glu Leu Val Ile His Glu Lys Gly
50                  55                  60

Phe Tyr Tyr Ile Tyr Ser Gln Thr Tyr Phe Arg Phe Gln Glu Glu Ile
65                  70                  75                  80

Lys Glu Asn Thr Lys Asn Asp Lys Gln Met Val Gln Tyr Ile Tyr Lys
                85                  90                  95

Tyr Thr Ser Tyr Pro Asp Pro Ile Leu Leu Met Lys Ser Ala Arg Asn
            100                 105                 110

Ser Cys Trp Ser Lys Asp Ala Glu Tyr Gly Leu Tyr Ser Ile Tyr Gln
        115                 120                 125

Gly Gly Ile Phe Glu Leu Lys Glu Asn Asp Arg Ile Phe Val Ser Val
130                 135                 140

Thr Asn Glu His Leu Ile Asp Met Asp His Glu Ala Ser Phe Phe Gly
145                 150                 155                 160

Ala Phe Leu Val Gly
                165
```

<210> SEQ ID NO 16
<211> LENGTH: 281
<212> TYPE: PRT
<213> ORGANISM: Homo sapiens

<400> SEQUENCE: 16

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Leu Pro
50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 17
<211> LENGTH: 155
<212> TYPE: PRT
<213> ORGANISM: Artificial Sequence
<220> FEATURE:
<223> OTHER INFORMATION: fragment of SEQ ID NO: 16

<400> SEQUENCE: 17

Leu Glu Lys Gln Ile Gly His Pro Ser Pro Pro Pro Glu Lys Lys Glu
1               5                   10                  15

Leu Arg Lys Val Ala His Leu Thr Gly Lys Ser Asn Ser Arg Ser Met
            20                  25                  30

Pro Leu Glu Trp Glu Asp Thr Tyr Gly Ile Val Leu Leu Ser Gly Val
            35                  40                  45

Lys Tyr Lys Lys Gly Gly Leu Val Ile Asn Glu Thr Gly Leu Tyr Phe
 50                  55                  60

Val Tyr Ser Lys Val Tyr Phe Arg Gly Gln Ser Cys Asn Asn Leu Pro
 65                  70                  75                  80

Leu Ser His Lys Val Tyr Met Arg Asn Ser Lys Tyr Pro Gln Asp Leu
                85                  90                  95

Val Met Met Glu Gly Lys Met Met Ser Tyr Cys Thr Thr Gly Gln Met
            100                 105                 110

Trp Ala Arg Ser Ser Tyr Leu Gly Ala Val Phe Asn Leu Thr Ser Ala
            115                 120                 125

Asp His Leu Tyr Val Asn Val Ser Glu Leu Ser Leu Val Asn Phe Glu
            130                 135                 140

Glu Ser Gln Thr Phe Phe Gly Leu Tyr Lys Leu
145                 150                 155

<210> SEQ ID NO 18
<211> LENGTH: 290
<212> TYPE: PRT
<213> ORGANISM: Homo sapiens

<400> SEQUENCE: 18

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

```
Phe Ile Phe Arg Leu Arg Lys Gly Arg Met Met Asp Val Lys Lys Cys
                260                 265                 270

Gly Ile Gln Asp Thr Asn Ser Lys Gln Ser Asp Thr His Leu Glu
            275                 280                 285

Glu Thr
    290

<210> SEQ ID NO 19
<211> LENGTH: 273
<212> TYPE: PRT
<213> ORGANISM: Homo sapiens

<400> SEQUENCE: 19

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
    115                 120                 125

His Ile Leu Lys Val Pro Glu Thr Asp Glu Val Glu Leu Thr Cys Gln
130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
    195                 200                 205

Leu Gln Ser Gln Met Glu Pro Arg Thr His Pro Thr Trp Leu Leu His
210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile

<210> SEQ ID NO 20
<211> LENGTH: 5
<212> TYPE: PRT
<213> ORGANISM: Artificial Sequence
<220> FEATURE:
<223> OTHER INFORMATION: linker
```

<400> SEQUENCE: 20

Gly Gly Gly Gly Ser
1               5

<210> SEQ ID NO 21
<211> LENGTH: 5
<212> TYPE: PRT
<213> ORGANISM: Artificial Sequence
<220> FEATURE:
<223> OTHER INFORMATION: linker

<400> SEQUENCE: 21

Gly Gly Gly Gly Ser
1               5

<210> SEQ ID NO 22
<211> LENGTH: 37
<212> TYPE: PRT
<213> ORGANISM: Artificial Sequence
<220> FEATURE:
<223> OTHER INFORMATION: linker

<400> SEQUENCE: 22

Gly Asp Pro Leu Val Thr Ala Ala Ser Val Leu Glu Phe Gly Gly Ser
1               5                   10                  15

Gly Gly Gly Ser Glu Gly Gly Gly Ser Glu Gly Gly Gly Ser Glu Gly
            20                  25                  30

Gly Gly Ser Asp Ile
        35

<210> SEQ ID NO 23
<211> LENGTH: 15
<212> TYPE: PRT
<213> ORGANISM: Artificial Sequence
<220> FEATURE:
<223> OTHER INFORMATION: hinge region of human IgG1

<400> SEQUENCE: 23

Glu Pro Lys Ser Cys Asp Lys Thr His Thr Cys Pro Pro Cys Pro
1               5                   10                  15

<210> SEQ ID NO 24
<211> LENGTH: 247
<212> TYPE: PRT
<213> ORGANISM: Artificial Sequence
<220> FEATURE:
<223> OTHER INFORMATION: linker

<400> SEQUENCE: 24

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala

```
                100                 105                 110
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Glu Pro Lys Ser Cys Asp Lys Thr
225                 230                 235                 240

His Thr Cys Pro Pro Cys Pro
                245

<210> SEQ ID NO 25
<211> LENGTH: 232
<212> TYPE: PRT
<213> ORGANISM: Artificial Sequence
<220> FEATURE:
<223> OTHER INFORMATION: linker

<400> SEQUENCE: 25

Glu Pro Lys Ser Ser Asp Lys Thr His Thr Ser Pro Pro Ser Pro Ala
1               5                   10                  15

Pro Pro Val Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
```

```
                210                 215                 220
Ser Leu Ser Leu Ser Pro Gly Lys
225                 230

<210> SEQ ID NO 26
<211> LENGTH: 27
<212> TYPE: PRT
<213> ORGANISM: Artificial Sequence
<220> FEATURE:
<223> OTHER INFORMATION: trimerization sequence

<400> SEQUENCE: 26

Gly Tyr Ile Pro Glu Ala Pro Arg Asp Gly Gln Ala Tyr Val Arg Lys
1               5                   10                  15

Arg Gly Glu Trp Val Leu Leu Ser Thr Phe Leu
            20                  25

<210> SEQ ID NO 27
<211> LENGTH: 24
<212> TYPE: PRT
<213> ORGANISM: Artificial Sequence
<220> FEATURE:
<223> OTHER INFORMATION: trimerization sequence

<400> SEQUENCE: 27

Val Thr Thr Leu Gln Asp Ser Ile Arg Lys Val Thr Glu Glu Asn Lys
1               5                   10                  15

Glu Leu Ala Asn Glu Leu Arg Arg
            20

<210> SEQ ID NO 28
<211> LENGTH: 13
<212> TYPE: PRT
<213> ORGANISM: Artificial Sequence
<220> FEATURE:
<223> OTHER INFORMATION: Mouse MOG 38-50 peptide

<400> SEQUENCE: 28

Gly Trp Tyr Arg Ser Pro Phe Ser Arg Val Val His Leu
1               5                   10
```